(12) United States Patent
Hadden

(10) Patent No.: US 7,182,942 B2
(45) Date of Patent: Feb. 27, 2007

(54) VACCINE IMMUNOTHERAPY FOR IMMUNE SUPPRESSED PATIENTS

(75) Inventor: John W. Hadden, Cold Spring Harbor, NY (US)

(73) Assignee: IRx Therapeutics, Inc., New York, NY (US)

( * ) Notice: Subject to any disclaimer, the term of this patent is extended or adjusted under 35 U.S.C. 154(b) by 279 days.

(21) Appl. No.: 10/637,869

(22) Filed: Aug. 8, 2003

(65) Prior Publication Data

US 2004/0071658 A1 Apr. 15, 2004

Related U.S. Application Data

(63) Continuation-in-part of application No. 10/015,123, filed on Oct. 26, 2001.

(60) Provisional application No. 60/243,912, filed on Oct. 27, 2000.

(51) Int. Cl.
*A61K 45/00* (2006.01)

(52) U.S. Cl. .................... 424/85.2; 424/85.1; 424/85.4; 424/85.6; 424/85.7; 514/2; 514/110; 514/176; 514/420

(58) Field of Classification Search .................... 424/85.2, 424/85.1, 85.4, 85.5, 85.6, 85.7; 514/2, 110, 514/176, 420
See application file for complete search history.

(56) References Cited

U.S. PATENT DOCUMENTS

| | | | |
|---|---|---|---|
| 4,116,951 A | 9/1978 | Wang | |
| 4,353,821 A | 10/1982 | Birr et al. | |
| 4,390,623 A | 6/1983 | Frabricius et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,464,355 A | 8/1984 | Fabricius et al. | |
| 4,466,918 A | 8/1984 | Birr et al. | |
| 4,470,926 A | 9/1984 | Birr et al. | |
| 4,475,196 A | 10/1984 | La Zor | |
| 4,486,194 A | 12/1984 | Ferrara | |
| 4,487,603 A | 12/1984 | Harris | |
| 4,612,365 A | 9/1986 | Birr et al. | |
| 4,910,296 A | 3/1990 | Birr et al. | |
| 4,925,678 A | 5/1990 | Ranney | |
| 4,959,217 A | 9/1990 | Sanders et al. | |
| 5,100,664 A | 3/1992 | Doyle et al. | |
| 5,167,616 A | 12/1992 | Haak et al. | |
| 5,169,383 A | 12/1992 | Gyory et al. | |
| 5,225,182 A | 7/1993 | Sharma | |
| 5,503,841 A | 4/1996 | Doyle et al. | |
| 5,632,983 A | 5/1997 | Hadden | |
| 5,643,565 A | 7/1997 | Doyle et al. | |
| 5,698,194 A | 12/1997 | Hadden | |
| 5,800,810 A | 9/1998 | Doyle et al. | |
| 6,060,068 A | 5/2000 | Doyle et al. | |

2002/0034494 A1 3/2002 Vicari, et al.

FOREIGN PATENT DOCUMENTS

EP 0 974 357 A1 7/1998

OTHER PUBLICATIONS

Albert et al, Nature, vol. 392, pp. 86–89 (1998). Banchereau et al, Annual Reviews of Immunology, vol. 18, pp. 767–811 (2000).
Barrera J, Verastegui E, Meneses A, Zinser J, de la Garza J, Hadden JW. Combination immunotherapy of squamous cell head and neck cancer: A phase 11 trial. Arch Otolaryngol Head Neck Surg 126:345–351 (2000).
Bellone, et al, Immunology Today, vol. 20, No. 10, p 457–462 (1998).
Berd D, Mastrangelo M J. Effect of low dose cyclophosphamide on the immune system of cancer patients: reduction of T suppressor function without depletion of the CD8+ subset. Cancer Research 47:3317–3321 (1987).
Borysiewickz L K, Fiander A. Nimako M. A recombinant vaccine virus encoding human papilomavirus type 16 and 18, E6 and E7 proteins as immunotherapy for cervical cancer. Lancet 347:1524–1527 (1996).
Burke and Olson, "Preparation of Clone Libraries in Yeast Artificial–Chromosome Vectors" in Methods in Enzymology, vol. 194, "Guide to Yeast Genetics and Molecular Biology", eds. C. Guthrie and G. Fink, Academic Press, Inc., Chap. 17, pp. 251–270 (1991).
Capecchi, "Altering the genome by homologous recombination" Science 244:1288–1292 (1989).
Cregg J M, Vedvick T S, Raschke W C: Recent Advances in the Expression of Foreign Genes in Pichia pastoris, Bio/Technology 11:905–910 (1993).
Dickinson et al., "High frequency gene targeting using insertional vectors", Human Molecular Genetics, vol. 2, No. 8, pp. 1299–1302 (1993).

(Continued)

Primary Examiner—Leon B. Lankford, Jr.
(74) Attorney, Agent, or Firm—Kohn & Associates, PLLC; Kenneth I. Kohn

(57) ABSTRACT

A method of immunotherapy to treat cancer or a synergistic anti-cancer treatment by administering an effective amount of a natural cytokine mixture (NCM), an effective amount of cyclophosphamide (CY), or an effective amount of indomethacin (INDO), wherein the NCM, CY, or INDO are administered singly or in combinations thereof. An anti-metastatic treatment method by promoting differentiation and maturation of immature dendritic cells in a lymph node; allowing presentation thereof; and preventing development of metastasis. A method of using an NCM as a diagnostic skin test for predicting treatment outcome. A method of pre-treating dendritic cells (DC) and a method of treating monocyte defects characterized by sinus histiocytosis or a negative NCM skin test. Compositions and methods for eliciting an immune response to endogenous or exogenous tumor antigens.

1 Claim, 11 Drawing Sheets

OTHER PUBLICATIONS

Duff and Lincoln, "Insertion of a pathogenic mutation into a yeast artificial chromosome containing the human APP gene and expression in ES cells", Research Advances in Alzheimer's Disease and Related Disorders (1995).

Gilboa, E, Eglitis, M A, Kantoff, P W, Anderson, W F: Transfer and expression of cloned genes using retroviral vectors. BioTechniques 4(6):504–512 (1986). Gillis et al. (1978).

Hadden JW, Endicott J, Baekey P, Skipper P, Hadden E M. Interleukins and contrasuppression induce immune regression of head and neck cancer. Arch Otolaryngol Head Neck Surg. 120:395–403 (1994).

Hadden JW, Saha A R, Sosa M, Hadden E M. Immunotherapy with natural interleukins and/or Thymosin α1 potently augments T lymphocyte responses of hydrocortisone–treated aged mice. Int'l J Immunopharmacol 17:821–828 (1995).

Hadden JW. Immunology and immunotherapy of breast cancer: An update: Int'l J Immunopharmacol 21:79–101 (1999).

Hadden JW. The immunopharmacology of head and neck cancer: An update. Int'l J Immunopharmacol 11/12:629–644 (1997).

Hadden JW. The treatment of zinc deficiency is an immunotherapy. Int'l J Immunopharmacol 17:696–701 (1995).

Hadden, J., E. Verastegui, J.L. Barrera, M. Kurman, A. Meneses, J.W. Zinser, J. de la Garza, and E. Hadden, "A trial of IRX–2 in patients with squamous cell carcinomas of the head and neck," International Immunopharmacology 3; 1073–1081 (2003).

Hadden, John W. "Immunodeficiency and cancer: prospects for correction," Intl. Immunopharm. 3:1061–1071 (2003).

Hadden, John W. "Combination immunotherapy," Intl. Immunopharm. 3:1049–1050 (2003).

Hank A J, Albertini M R, Sondel P M. Monoclonal antibodies, cytokines and fusion proteins in the treatment of malignant disease. Cancer Chemother & Biol Resp Mod 18:210–222 (1999).

Hirsch B, Johnson JT, Rabin BD, et al. Immunostimulation of patients with head and neck cancer. Arch Otolaryngol 1983; 109:298–301.

Huston et al, "Protein engineering of single–chain Fv analogs and fusion proteins" in Methods in Enzymology (J J Langone, ed.; Academic Press, New York, N.Y.) 203:46–88 (1991).

Huxley et al., "The human HPRT gene on a yeast artificial chromosome is functional when transferred to mouse cells by cell fusion", Genomics, 9:742–750 (1991).

Jakobovits et al., "Germ–like transmission and expression of a human–derived yeast artificial chromosome", Nature, vol. 362, pp. 255–261 (1993).

Johnson and Bird, 1991 Construction of single–chain Fvb derivatives of monoclonal antibodies and their production in *Escherichia coli* in Methods in Enzymology (J J Langone, ed.; Academic Press, New York, N.Y.) 203:88–99 (1989).

Kavanaugh D Y, Carbone D P. Immunologic dysfunction in cancer. Hematol–Oncol Clinics of North Amer 10(4):927–951 (1996).

Lamb et al., "Introduction and expression of the 400 kilobase precursor amyloid protein gene in transgenic mice", Nature Genetics, vol. 5, pp. 22–29 (1993).

Maass G, Schmidt W, Berger M, et al. Priming of tumor–specific T–cells in the draining lymph nodes after immunization with interleukin 2–secreting tumor cells: three consecutive stages may be rquired for successful tumor vaccination. Proc Natl Acad Sci USA, 92:5540–5542 (1995).

Mackall (Stem Cells 2000, vol. 18. pp. 10–18) Mackall et al, (New England Journal of Medicine, vol. 332, pp. 143–149 (1995).

Maclean G D, Miles D W, Rubens R D, Reddish M A, Longenecker bone marrow. Enhancing the effect of Theratope STn–KLH cancer vaccine in patients with metastatic breast cancer by pretreatment with low–dose intravenous cyclophosphamide. J Immunother Emphasis Tumor Immunol 19(4):309–316 (1996).

Marshak et al, "Strategies for Protein Purification and Characterization. A laboratory course manual." CSHL Press (1996).

Masek, K. et al., "Neuroendocrine immune interactions in health and disease," Intl. Immunopharm. 3:1235–1246 (2003).

Meneses A, Verastegui E, Barrera J L, Zinser J, de la Garza J, Hadden J W. Histological findings in patients with head and neck squamous cell carcinoma receiving perilympatic natural cytokine mixture prior to surgery. Arch Pathol Lab Med 122:447–454 (1998).

Meneses A, Verastegui E, Barrera J L, de la Garza J, and Hadden J W, "Lymph node histology in head and neck cancer: impact of immunotherapy with IRX–2," International Immunopharmacology, 3; 1083–1091 (2003).

Mernaugh and Mernaugh, "An overview of phage–displayed recombinant antibodies" in Molecular Methods In Plant Pathology (R P Singh and U S Singh, eds.; CRC Press Inc., Boca Raton, Fla.) pp. 359–365 (1995).

Mishell and Shiigi (Selected Methods in Cellular Immunology 1981).

Murphy G P, Tjoa B A, Simmons S J. The prostate. 38:43–78 (1999).

Naylor, Paul H. et al., "T cell targeted immune enhancement yields effective T cell adjuvants," Intl. Immunopharm. 3:1205–1215 (2003).

Pearson and Choi, Expression of the human b–amyloid precursor protein gene from a yeast artificial chromosome in transgenic mice. Proc. Natl. Acad. Sci. USA, 90:10578–82 (1993).

Roitt I, Brostoff J, Male D. Immunology, JB Lippincott Co, Phila, Pa., (1989).

Rothstein, "Targeting, disruption, replacement, and allele rescue: integrative DNA transformation in yeast" in Methods in Enzymology, vol. 194, "Guide to Yeast Genetics and Molecular Biology", eds. C. Guthrie and G. Fink, Academic Press, Inc., Chap. 19, pp. 281–301 (1991).

Saha A, Hadden E M, Hadden J W. Zinc induces thymulin secretion from human thymic epithelial cells in vitro and augments splenocytes and thymocyte response in vivo. Int'l J Immunopharmacol 17:729–734 (1995).

Sahin U, Tureci O, Pfreundschuh. Serological identification of human tumor antigens. Curr Opin Immunol 9:709–715 (1997).

Sanda M G, Smith D C, Charles L G. Recombinant vaccinia–PSA (Prostvac) can include a prostate–specific immune response in androgen–modulated human prostate cancer. Urology 52:2 (1999).

Schedl et al., "A yeast artificial chromosome covering the tyrosinase gene confers copy number–dependent expression in transgenic mice", Nature, vol. 362, pp. 258–261 (1993).

Signorelli, Kathy L. et al., "T cell immunostimulation by methyl inosine 5'-monophosphate: application to infectious diseases," Int. Immunopharm. 3:1177–1186 (2003).

Sprent, et al, Science, vol. 293, 245–248 (2001).

Strauss et al., "Germ line transmission of a yeast artificial chromosome spanning the murine a1 (I) collagen locus", Science, vol. 259, pp. 1904–1907 (1993).

Tagawa M. Cytokine therapy for cancer. Current Pharmaceut Design 6(6):681–699 (2000).

Valente G, DeStefani A, Jemma C, Giovarelli M, Geuna N, Cortesina G, Forni G, Palestro G. Infiltrating leukocyte populations and T–lymphocyte subsets in head and neck squamous cell carcinomas from patients receiving perilymphatic injections of recombinant interleukin–2. A pathologic and immunophenotypic study. Modern Pathol 3(6):702–708 (1990).

Van der Eynde B, Van der Bruggen, T cell defined tumor antigens. Curr Opin Immunol 9:684–693 (1997).

Verastegui E, Barrera J L, Zinzer J, del Rio R, Meneses A, de la Garza J, Hadden J W. A natural cytokine mixture (IRX–2) and interference with immune suppression induce immune mobilization and regression of head and neck cancer. Int'l J Immunopharmacol 11/12:619–627 (1997).

Verastegui, Emma L. et al., "Long–term immune dysfunction after radiotherapy to the head and neck area," Intl. Immunopharm. 3:1093–1104 (2003).

Wang R F, Rosenberg S A. Human tumor antigens for cancer vaccine development. Immunologic Reviews 170:85–100 (1999).

Weber J. Tumor vaccines. Medscape Anthology 3:2 (2000).

Whiteside, et al, Cancer Res. 53:5654–5662, (1993).

Wolf et al, Arch. Oto. Laryngol. 111:716–725 (1985).

Meneses, Abelardo, et al., "Histologic Findings in Patients with Head and Neck Squamous Cell Carcinoma Receiving Perilymphatic Natural Cytokine Mixture (IRX–2) Prior to Surgery," *Arch Pathol Lab Med,* vol. 122:447–454 (1998).

Hadden, John W. et al., "Interleukins and Contrasuppression Induce Immune Regression of Head and Neck Cancer," *Arch Otolaryngol Head Neck Surg.,* vol. 120:395–403 (1994).

Hadden, J. et al., "A trial of IRX–2 in patents with squamous cell carcinomas of the head and neck," *International Immunopharmacology,* 3:1073–1081 (2003).

Barrera, Jose Luis, et al., "Combination Immunotherapy of Squamous Cell Carcinoma of the Head and Neck," *Archives of Otolaryngology –Head & Neck Surgery,* 126,3:345–351 (2000).

VACCINE IMMUNOTHERAPY FOR IMMUNE SUPPRESSED PATIENTS

CROSS-REFERENCE TO RELATED APPLICATIONS

This application is a continuation-in-part of U.S. patent application Ser. No. 10/015,123, filed Oct. 26, 2001, which claims the benefit of priority under 35 U.S.C. Section 119(e) of U.S. Provisional Patent Application No. 60/243,912, filed Oct. 27, 2000, both of which are incorporated herein by reference.

BACKGROUND OF THE INVENTION

1. Technical Field

The present invention relates to vaccine therapy for cancer patients. More specifically, the present invention relates to a vaccine immunotherapy, which immunizes cancer patients, having immune suppression, to both endogenous and exogenous tumor peptides or proteins.

2. Background Art

It has become increasingly apparent that human cancers have antigens, which, if reacted upon by the host's immune systems, lead to tumor regression. These antigens have been defined by both serological and cellular immune approaches. This has lead to the definition of both B and T cell epitopes (Sahin U, et al, Curr Opin Immunol 9:709–715, 1997; Van der Eynde, B, et al. Curr Opin Immunol 9:684–693, 1997; Wang R F, et al., Immunologic Reviews 170:85–100, 1999). Based upon these results, it has become a goal of cancer immunotherapists to induce regressions of tumors. However, historically, successful efforts have been sporadic and generally minor in frequency and magnitude.

A fundamental problem in the effort to immunize cancer patients is that the tumor-bearing state is associated with immunosuppressive mechanisms derived from both the tumor and the host's disturbed immune system (Kavanaugh D Y, et al, Hematol-Oncol Clinics of North Amer 10(4):927–951, 1996), thereby making immunization difficult and until now impossible on a consistent basis. Immune suppression or depletion involves a reduced capacity of the immune system to respond. Such suppression can be drug or disease induced. The condition can be drug induced by treatment, virus induced as in AIDS, or induced by a disease state such as cancer. The immune system in this condition is effectively turned off.

A variety of tumor immunization strategies have been developed. However, all of these strategies are complex and deviate significantly from the conventional immunization strategies used for infectious diseases (Weber J. Tumor, Medscape Anthology 3:2, 2000). One such tumor immunization strategy involves Theratope(R), a Sialyl TN polysaccharide mucin antigen conjugated with keyhole limpet hemocyanine and administered with Detox(R) mycobacterium adjuvant and low dose cyclophosphamide (Maclean G D, et al, J Immunother Emphasis Tumor Immunol 19(4):309–316, 1996). However, use of this vaccine in patients with metastatic breast and ovarian cancer has yielded major clinical responses in a low percentage of patients. A major response means greater than 50% tumor reduction.

Gene therapy has also been attempted using an adenovirus construct as an expression vector for genes expressing Papilloma virus peptide 16 has been used for immunization or patients with cervical cancer and has yielded major clinical responses in a low percentage of patients (Borysiewickz L K, et al, Lancet 347:1524–1527, 1996).

Dendritic cell mediated therapy has also been attempted, wherein dendritic cells were pulsed with oligopeptide fragments of prostate specific antigens (PSA). Prostate specific membrane antigen (PSMA) has been used in patients with metastatic prostate cancer with major clinical responses in a low percentage of patients (Sanda M G, et al, Urology 52:2, 1999; Murphy G P, et al, The prostate. 38:43–78, 1999).

Additionally, autologous tumors have been used with low dose cyclophosphamide and BCG to immunize cancer patients with malignant melanoma. However, few clinical responses were reported (Mastrangelo M J, et al, Seminars in Oncology 23(6):773–781, 1996). Another strategy attempted included using MAGE antigens with a variety of vaccine adjuvants. Again, this has yielded few, if any, responses in patients with malignant melanoma (personal communication Thierry Boon).

Several patents to Doyle et al (U.S. Pat. Nos. 5,503,841; 5,800,810; 6,060,068; 5,643,565; 5,100,664) disclose methods of enhancing the immune response in patients using Interleukin 2-(IL-2). This method is disclosed for use in response to infectious diseases and primarily functions using antigens known to be immunogenic. Limited applicability was demonstrated. As disclosed above, the treatment of cancer is known to require different approaches. To date, treatment with IL-2 has shown minor effects in two cancers, renal cell and malignant melanoma (response rates less than 20%). It is generally considered ineffective in squamous cell head and neck and cervical cancer and in prostate cancer. Hence, it is not approved for these uses. It would therefore not be within the skill of one in the art to apply the method of the Doyle et al patents to the use of small peptides in the treatment of cancer.

It is important to contrast prevention with known "classic" antigens of complex structure and high molecular weights in healthy patients vs. treatment (generally unsuccessful) with tumor antigens or peptides (general unsuccessful) in immunosupressed patients (generally unsuccessful). The first is easy and our current viral vaccines attest to their efficacy. The latter is nearly impossible on a routine basis despite 30 years of intense effort.

It is important that this invention relates to, but not exclusively to, immunizing with endogenous peptide processed and presented by dendritic cells or endogenously administered to an environment (lymph node) where dendritic cells have been prepared and can present them to T-cells effectively. This goal is considered by many immunologists to be insurmountable. Peptides are much too small to be effective immunogens, their one half life is short they are often non-mutated self antigens to which the patient is immunologically tolerant and gaining a response is tantamount to inducing auto immunity.

In several of the above strategies, cellular and/or tumoral immunity to tumor-associated antigens has been induced (Weber J. Tumor, Medscape Anthology 3:2, 2000; Maclean G D, et al, J Immunother Emphasis Tumor Immunol 19(4):309–316, 1996; Borysiewickz L K, et al, Lancet 347:1524–1527, 1996; Sanda M G, et al, Urology 52:2, 1999). This is especially so in association with tumor regression. Nevertheless, the success rate of such treatments is negligible and inconsistent (<30%).

It would therefore be useful to develop a consistent and effective method of immunizing cancer patients.

SUMMARY OF THE INVENTION

According to the present invention, there is provided a method of immunotherapy to treat cancer by administering an effective amount of a natural cytokine mixture (NCM) including, but not limited to, IL-1, IL-2, IL-6, IL-8, IL-12, IFN-δ, TNF-α, GM-CSF, G-CSF, recombinants thereof, and combinations thereof. Further, the present invention provides a method of immunotherapy to treat cancer by administering an effective amount of cyclophosphamide (CY) and an effective amount of indomethacin (INDO). Various anti-cancer treatment methods are also provided wherein administration of an effective amount of CY occurs along with an effective amount of a nonsteroidal anti-inflammatory drug (NSAID) including, but not limited to, indomethacin (INDO), Ibuprofen, celecoxib (Celebrex®), rofecoxib (Vioxx®), CoxII inhibitors, and combinations thereof. More specifically, the present invention provides a method of immunotherapy to treat cancer by administering an effective amount of a CY in combination with an effective amount of INDO and an effective amount of IFN-δ, IL-2, IL-1, and TNF-α. Additionally, the present invention provides a method of immunotherapy to treat cancer by administering an effective amount of a CY in combination with an effective amount of INDO and an effective amount of recombinant IL-2, recombinant TFN-δ, recombinant TFN-α, and recombinant IL-1. The present invention further provides a synergistic anti-cancer treatment by administering an effective amount of CY and INDO in combination with an NCM described herein. In addition, the present invention provides an anti-metastatic treatment method by promoting differentiation and maturation of immature dendritic cells in a lymph node; allowing presentation by resulting mature dendritic cells of antigen to T-cells to gain immunization of the T-cells to the antigen; and preventing development of metastasis. Alternatively, the present invention provides an anti-metastatic method by unblocking immunization at a lymph node; and generating systemic immunity. The present invention also provides a skin test and a method of pre-treatment of dendritic cells (DC) by applying an effective amount of CY and INDO in combination with an NCM described herein. The present invention further provides a method of treating monocyte defects characterized by sinus histiocytosis or a negative NCM skin test by applying an effective amount of CY and INDO in combination with an NCM described herein. Finally, the present invention provides compositions and methods for eliciting an immune response to endogenous or exogenous tumor antigens.

BRIEF DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
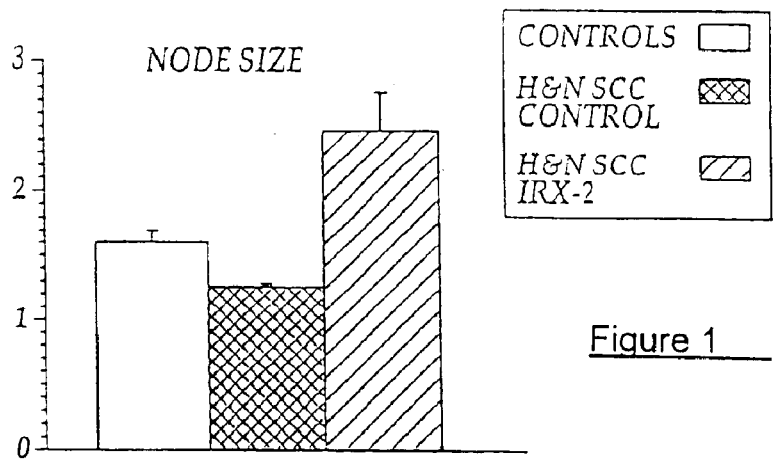
FIG. 1 is a bar graph showing lymph node size in controls, and cancer controls or IRX-2(NCM) treated populations with squamous cell head & neck cancer (H&NSCC)
Figure 2A:
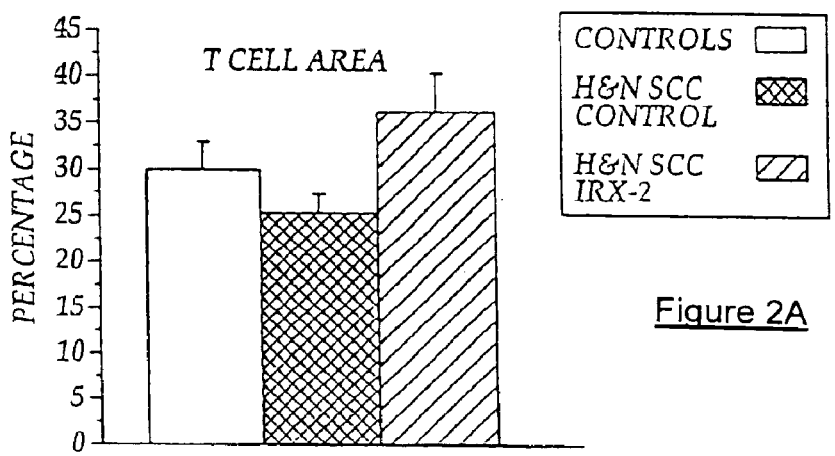
FIG. 2 shows two bar graphs, one showing T-cell area and the second showing density in controls and head and neck squamous cancer controls and patients treated with NCM (IRX-2)
Figure 2B:
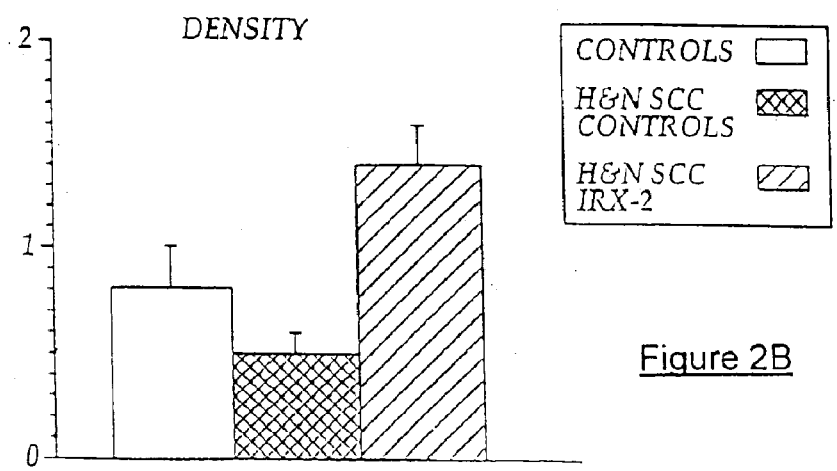
Figure 3A:
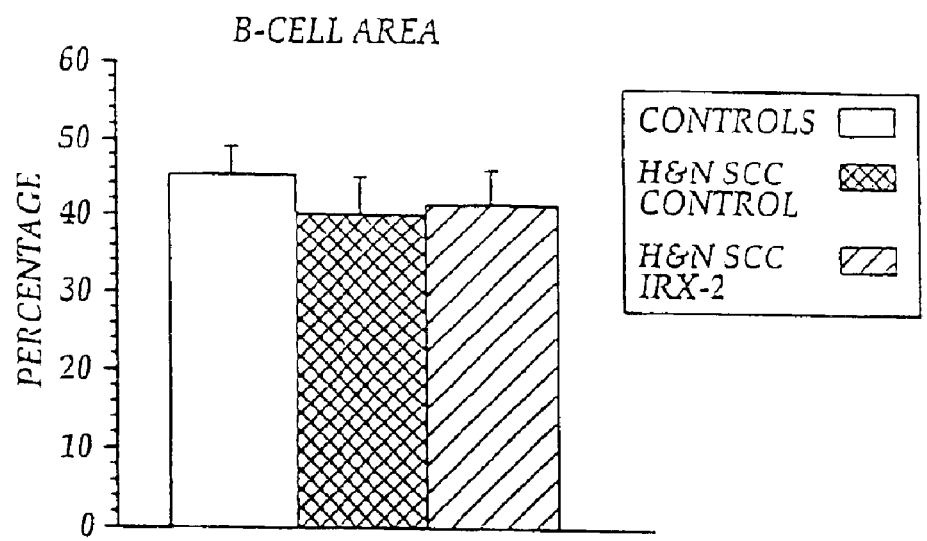
FIG. 3 shows two bar graphs showing B-cell area and follicles in the three treatment groups.
Figure 3B:
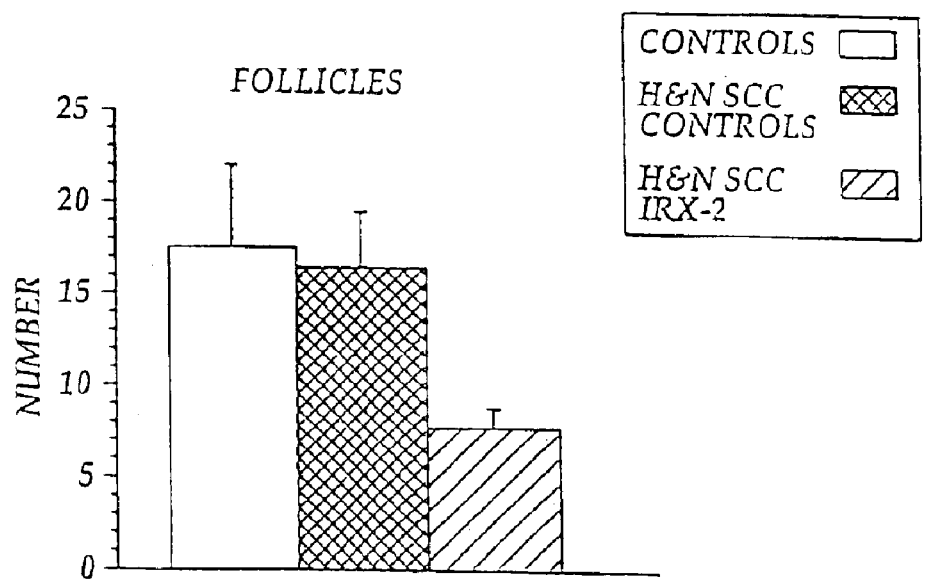
Figure 4A:
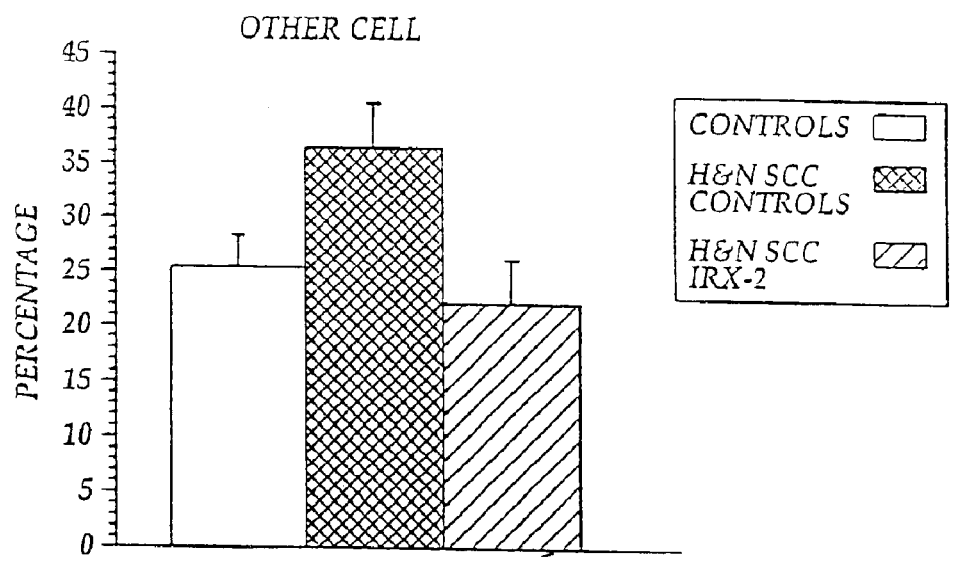
FIG. 4 shows a comparison of other cells and sinus histiocytosis in the three treatment groups.
Figure 4B:
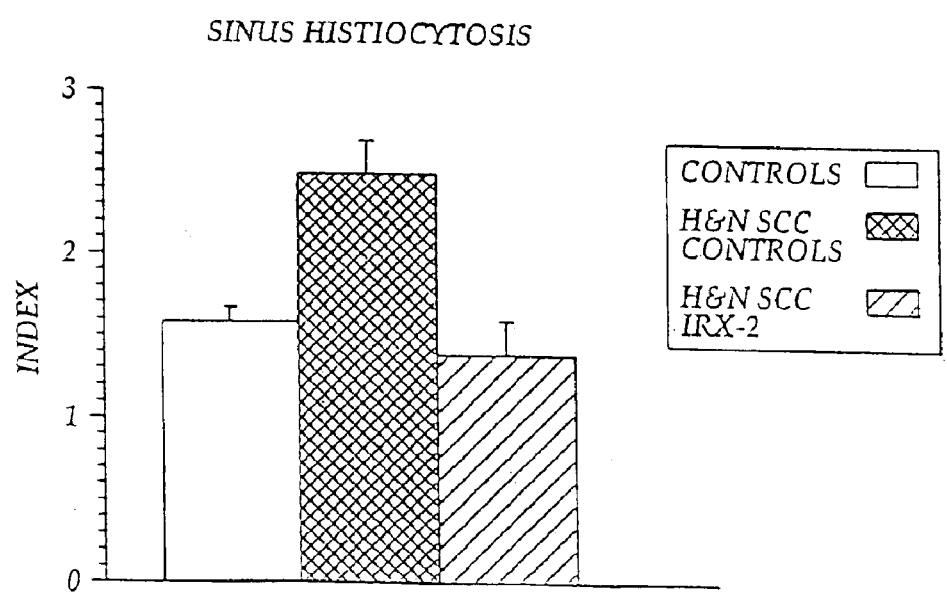

Generally, the present invention provides methods for treating patients utilizing vaccine immunotherapy wherein the patients are immune suppressed. By immune suppressed, it is meant that the patient has reduced cellular immunity and thus impaired capacity to respond to new antigens. More specifically, in blood, T lymphocyte counts are reduced and/or function of these cells is impaired, as shown, e.g. by PHA proliferation assay.

By "adjuvant" it is meant a composition with the ability to enhance the immune response to a particular antigen. To be effective, an adjuvant must be delivered at or near the site of antigen. Such ability is manifested by a significant increase in immune mediated protection. Enhancement of immunity is typically manifested by a significant increase (usually greater than 10 fold) in the titer of antibody raised to the antigen. Enhancement of cellular immunity can be measured by a positive skin test, cytotoxic T-cell assay, ELISPOT assay for δIFN or IL-2, or T-cell infiltration into the tumor (as described below).

By "tumor associated antigen", it is meant an analogous protein or peptide (which were previously shown to work by pulsing of dendritic cell ex vivo) or other equivalent antigen. This can include, but is not limited to PSMA peptides, MAGE peptides (Sahin U, et al, Curr Opin Immunol 9:709–715, 1997; Wang R F, et al, Immunologic Reviews 170:85–100, 1999), Papilloma virus peptides (E6 and E7), MAGE fragments, NY ESO-1 or other similar antigens. Previously, these antigens were not considered to be effective in treating patients based either on their size, i.e. they are too small or that they were previously thought to not have the immunogenic properties (i.e., self antigens).

By "NCM," it is meant as a natural cytokine mixture, as defined and set forth in U.S. Pat. Nos. 5,632,983 and 5,698,194. The NCM can include recombinant cytokines. Briefly, NCM is prepared in the continuous presence of a 4-aminoquinolone antibiotic and with the continuous or pulsed presence of a mitogen, which in the preferred embodiment is PHA.

T lymphocytopenia (low T cell levels in blood) is a diagnostic characteristic of cellular immune deficiency, while impaired function of existing thymphocytes is the other characteristic. There is no generally accepted (clinically approved) way to treat T lymphocytopenia. Bone marrow transplants (+− thymus transplants) have been used in cases of severe combined immunodeficiency (SCID-congenital, irradiation or chemotherapy induced). Recombinant IL2 has been tried in AIDS with some effect by much toxicity.

There are two ways to make new T cells to attempt to correct T lymphocytopenia. One way, as in rIL-2 therapy, expands T cells already in the periphery, i.e., memory T cells (CD45RO) (blood, lymph node and spleen). The other involves processing in the thymus of new T cells from bone marrow-derived precursors. This happens naturally in children but not in adults. These new cells are called recent "thymic émigrés" and have the surface marker of "naive" T cells i.e., CD45RA. NCM therapy (plus Thymosin α1) results in the production of these new T cells as well as expanding preexisting memory T cells. More specifically, the present invention relates to immunization to provide an immune response to antigens, which is either endogenously or exogenously administered. Such antigens in the past may have been believed to be immunogenic while others used in the present invention may have been thought previously to be non-immunogenic. Any antigen can be used with the present invention. Examples of such antigens are EADPTGHSY (melanoma) from MAGE-1 protein, EVDPIGHLY (lung carcinoma) from MAGE-3, EVDPIGHLY (lung carcinoma) from MAGE-3, and many others. (See Bellone, et al, Immunology Today, Vol. 20, No. 10, p 457–462 (1999). The present invention is directed towards affecting antigen processing generally; therefore, any antigen can be used with the present invention. The present invention can extend to all forms of tumor antigens and haptens including peptides and/or carbohydrates. The present invention can extend to areas of applicability as in AIDS virus vaccine in HIV+ patients; other difficult to manage situations; renal transplants, aged individuals, and the like.

The present invention utilizes several general derived method steps for obtaining immunization in subjects where such immunization was previously thought to be impossible. More specifically, the present invention provides a method for overcoming immune depression by inducing production of naive T cells. The term "naive" T cells, is meant to mean newly produced T cells, even in adults, wherein these T cells have not yet been exposed to antigen. Such T cells at this stage are non-specific yet capable of becoming specific upon presentation by a mature dendritic cell having antigen, such as tumor peptides, exposed thereon. Thus, the present invention replenishes or generates new T cells. This is generally accomplished by administering a natural cytokine mixture (NCM). The NCM includes, but is not limited to, IL1, IL2, IL6, IL8, IL10, IL12, δIFN, TNFα, G- and GM-CSF, recombinants thereof, and combinations thereof. The amount and proportions of these constituents are detailed below. Preferably, about 150–600 units of IL2 are contained in the NCM.

In any embodiment, it is preferred that the NCM is injected around lymphatics that drain into lymph nodes regional to a lesion, such as a tumor or other persistent lesions being treated. Peritumoral injection has been associated with little response, even progression and is thus contraindicated. A ten (10) day injection scheme is optimal and a twenty (20) day injection protocol, while effective clinically, tends to reduce the TH1 response and shift towards a less desirable TH2 response as measured by lymphoid infiltration into the cancer. Bilateral injections are also effective. Where radical neck dissection has occurred, contralaterial injection is effective.

It is preferable to block endogenous suppression of T cells, such as caused by various cancer lesions. Blocking is effected by the co-delivery of low dose cyclophosphamide (CY) and a non-steroidal anti-inflammatory drug (NSAID). The NSAID of choice is indomethacin (INDO). While INDO is the most effective NSAID, it is also arguably the most toxic. Celebrex® and Vioxx®, Cox II NSAIDS, are also less effective. Ibuprofen was effective, but the histological responses were characteristic of a TH2 rather than TH1 mediated response, this being less desirable. Side effects of NSAIDS are to be aggressively treated with proton inhibitors and a prostaglandin E analog. Zinc and multivitamins are useful agents to help restore T cell immunity. Treatment with contrasuppression and zinc without the NCM is ineffective.

In summary, the minimum regimen is perilymphatic treatment with the NCM combined with contrasuppression using CY and an NSAID. The alternative regimen is the previously mentioned regimen further including zinc and vitamins, possibly including the addition of selenium. Preferable dosing of Zinc is 50 to 75 mg. A standard multivitamin can be administered. The zinc can be an available gluconate.

In order to maximize clinical response and for the greatest increase in survival rate, the degree and type of lymphocyte infiltration is important. Lymphocyte: granulocyte or macrophage infiltration of a 90:10 ratio is optimal. T and/or B cell infiltration preferably is diffuse and intense and not peripheral. Light infiltration of less than 20% is not associated with a robust clinical response. Tumor reduction and fragmentation in the histological samples is preferred in reflecting a good response. Lymph node changes key to good response involve at least five (5) aspects. Lymph node enlargement and not just reversal of tumor induced reduction of size but overall increase in size compared to normal is preferred. Increased T and B cell areas indicate an immunization. Sinus histocytosis (SH) is believed to be the accumulation of immature dendritic cells, which have ingested and processed tumor antigens but are unable to mature and present these tumor peptides to naive T cells capable of stimulating TH1 and TH2 effective cells which lead to cytotoxin T cell and B cells. Reversal of SH is preferred.

Thus, the present invention provides for unblocking immunization at a regional lymph node by promoting differentiation and maturation of immature dendritic cells in a regional lymph node and thus allowing presentation by resulting mature dendritic cells of small peptides, generally nine amino acids in length to T cells to gain immunization of the T cells. Additionally, induction of mature dendritic cells is required. Finally, mobilization of peripheral blood T-lymphocytes in T-lymphocytopoenic patients in the presence of induction of naive T cells capable of responding to dendritic cells presenting endogenous tumor peptides is desired. (See, Sprent, et al, Science, Vol 293, Jul. 13, 2001, pgs 245–248).

In view of the above, the key mechanistic features of the present invention are the in vivo maturation of dendritic cells resulting in effective peptide antigen presentation. Based on the examples presented below, increases in CD45 RA positive naive uncommitted T cells have been found. With antigen, this leads to T and B cell clonal expansion, creating immunity in the patient. The resulting infiltration into tumors by hematogenous spread leads to robust tumor destruction. The result, as found in the data below, is increased survival due to immunologic memory. (See, Sprent et al, cited above).

It is predicted logically that exogenously provided synthetic or extracted tumor peptides (See, Bellone, et al, cited above) can be delivered into the preprimed or co-primed regional or distal lymph node and yield tumor antigen specific T cells, with or without B cells. Three examples are set forth below. In view of the above, it can be concluded that the action of NCM plus other agents is useful as for any tumor antigens (synthetic and endogenous, peptides and proteins). Many of these peptides are not normally immunogenic and only when presented by a matured, activated dendritic cell, will they be effective in immunizing naive T cells. Thus, the appearance of an immune T cell means, de facto, that a dendritic cell has been made or allowed to work properly. Also de facto, dendritic cell activation and maturation is to be considered a key factor in cancer immunodeficiency as well as the well-known defects in T cells such as a decreased number and function with anergy and presumed apoptosis.

Referring more specifically to the protocol and medicant delivered in accordance with the present invention, the invention utilizes the NCM to immunize patients, such as cancer patients, as well as patients with other lesions or antigen producing disease conditions.

More specifically, the present invention utilizes a method of enhancing the immune response of cancer patients to a cancer by administering an effective amount of a composition containing therein the NCM and a tumor-associated antigen, wherein the NCM acts as an adjuvant to produce the immune response. The tumor-associated antigen can be either an endogenously processed tumor peptide preparation resident in regional nodes of patients with cancer or in conjunction with an exogenously administered tumor antigen preparation in or near these nodes. Tumor peptides, as well as antigens, are included herein even though peptides are not expected to be immunogenic where tumor associated protein antigens would more likely be more so since they are complete.

In the preferred embodiment, the composition of the present invention involves the administration of the NCM plus a tumor associated or specific antigen, as defined below with low doses of CY, a cyclooxygenase inhibitor, and other similar compounds which have been shown to further increase the effects of the composition of the present invention.

According to the present invention, there is provided an NCM that has been previously shown to be effective in promoting T cell development and function in aged, immunosuppressed mice. Upon administering this NCM to immunosuppressed patients with head and neck cancer, it is demonstrated in this application for the first time that the mobilization of T lymphocytes in the blood of cancer patients treated with the NCM produces an increase in immature, naive T cells bearing both CD2 and CD45 RA. This is one of the first demonstrations that adult humans can generate naive T cells. Previous references: Mackall et al, (New England Journal of Medicine (1995), Vol. 332, pp. 143–149) and a review by Mackall (Stem Cells 2000, Vol. 18. pp. 10–18) discusses the inability to generate new T cells in adults but not children, and discusses the problem of trying to replenish T cells following cancer chemotherapy and/or radiotherapy. In general, there is the dogma that new T cells are not generated in the adult human. However, following bone marrow transplantation for intense chemotherapy, there has been evidence that new T cells can be generated in the adult. No molecular therapy to date has been able to achieve this, although increases in lymphocytes counts have been achieved with prolonged and intense therapy with recombinant interleukin-2 in patients infected by HIV. These have not been clearly demonstrated to be thymus derived T cells and are presumably an expansion of pre-existing peripheral T cells.

Previously, Cortesina et al. employed a natural IL-2, perilymphatically in patients with head and neck cancer and induced several tumor regressions (Cortesina G, et al, Cancer 62:2482–2485, 1988) with some tumor infiltration with leukocytes (Valente G, et al, Modern Pathol 3(6):702–708, 1990). Untreatable recurrences occurred and the response was termed non-specific and without memory and thus nonimmunologic (Cortesina G, et al, Br J Cancer 69:572–577, 1994). The repeated attempts to confirm the initial observations with recombinant IL-2 were substantially unsuccessful (Hadden J W, Int'l J Immunopharmacol 11/12:629–644, 1997).

The method of the present invention involves using an NCM with local perilymphatic injections or other injections that are known to those of skill in the art to provide sufficient localization of the immunotherapy compound. In the preferred embodiment, the injections take place in the neck, but can be applied in other locations as required by the disease to be treated. This treatment induced clinical regressions in a high percentage of patients who also showed improved, recurrence free survival (Hadden J W, et al, Arch Otolaryngol Head Neck Surg. 120:395–403, 1994; Meneses A, et al, Arch Pathol Lab Med 122:447–454, 1998; Barrera J, et al, Arch Otolaryngol Head Neck Surg 126:345–351, 2000; Whiteside, et al, Cancer Res. 53:564–5662, 1993). Whiteside, et al (Cancer Res. 53:5654–5662, 1993) observed that in head and neck cancer, tumoral injection of recombinant interleukin-2 produced a T cell lymphocyte infiltrate, but without significant clinical responses. Peritumoral injection of Multikine (Celsci Website) (in combination with perilymphatic injection in up to 150 patients resulted in significant tumor responses, i.e. greater than 50% tumor reduction in only 11 patients, making their response rate less than 10% in contrast to the high degree of response observed in the present studies, 40%. In addition, they noted 50% non-responders where Applicants have observed only 20%.

Peritumoral and intratumoral injection can be associated with progression of disease even in patients who initially have had a positive response to the NCM protocol, thus undoing its benefit. Peritumoral injection is thus contraindicated and is excluded as part of the present invention. This has led to the interpretation that the tumor is not the site of immunization and the present application presents documentation that the regional lymph node is the site of immunization. Then, analysis of regional lymph nodes revealed data, which indicated that the regional lymph node is the site of immunization to postulated tumor antigens (FIGS. 14–18). With the identification of a number of different tumor antigens, it has been a conundrum over the last decade that given the presence of such antigens, they have not been employed effectively in immunization protocols. Sporadic positive examples have been reported, but in the main, the data are negative. The problem of antigen presentation has been focused on in the last decade and the dendritic cell has emerged as a critical player in the presentation of small peptides derived from tumors. See DeLaugh and Lotts, Current Opinion In Immunology, 2000, Vol. 12, pp.583–588; Banchereau et al, Annual Reviews of Immunology, (2000), Vol. 18, pp. 767–811; also Albert et al, Nature, Vol. 392, pp.86–89 (1998).

In brief, in order for tumor antigens to be properly antigenic, they must arrive from an apoptotic rather than a necrotic tumor cell (Albert, Nature, 39 2:86–87, 1997). They need to be captured by immature dendritic cells that have the morphology of large histocytes. These immature dendritic cells process antigen (endocytosis, phagocytosis and digestion) and evolve into mature dendritic cells, which display peptide fragments (generally nine amino acids) of the digested antigen in the MHC groove for presentation to T cells. T cells, in order to respond, must have antigen presented to them in the MHC groove plus various co-stimulatory signals.

Investigators, such as Murphy et al, 1999, have utilized dendritic cells generated in culture and then pulsed with tumor antigens and have achieved a small degree of success in immunizing patients against prostate specific membrane antigen peptides. Unfortunately, this approach of pulsing dendritic cells is cumbersome and has been rather inefficient. In the present invention, Applicants have shown that the cells present in the lymph node sinuses, which accumulate in cancer, are cells of the lineage of dendritic cells and that following the in vivo treatment with the NCM protocol of the present invention, these cells disappear and the antigen ultimately becomes immunogenic for T cells. They are able then to respond to the tumor. So an aspect of this invention is being able to generate a microenvironment in the regional lymph node, which allows effective antigen processing and presentation. The immunization, which derives results in T cells able to traffic to the lesion and destroy tumors, is de facto demonstration of adequate antigen processing by dendritic cells. Additionally, none of the patients treated with NCM developed distant metastasis, which is expected in up to 15% clinically and up to 50% pathologically. This indicates that a systemic immunity rather than merely a local immunity has been induced by the treatment. This is a drastic improvement over the compositions in the prior art, because the prior art compositions, at best, were inconsistently effective against metastatic disease. The ability of the composition of the present invention to create systemic immunity allows more effective and efficient treatment of a patient. Further, the magnitude of systemic response enables an individual to be administered smaller doses without limiting the effectiveness of the treatment and without toxicity.

The literature (Hadden J W, Int'l J Immunopharmacol 11/12:629–644, 1997; Hadden J W. Immunology and immunotherapy of breast cancer: An update: Int'l J Immunopharmacol 21:79–101, 1999) has indicated that for both SCC and adenocarcinomas, the two major types of cancer, regional lymph nodes reflect abnormalities related to the tumor, including sinus histocytosis, lymphoid depletion and often the presence of anergic tumor associated lymphocytes (capable of reacting to tumor cells with ex vivo expansion and recovery using IL2). Then, with metastases, lymphoid depletion and depressed function occur. Additionally, uninvolved cervical lymph nodes of such patients have shown a reduction in average size and an increase in sinus histocytosis associated with head and neck cancers. (See, FIGS. 1–4).

Specifically relating to the composition, the composition of the present invention involves the natural cytokine mixture plus either endogenous or exogenous tumor associated antigen. Additionally, low doses of CY, cyclooxygenase inhibitors, zinc, and other similar compounds have been shown to further increase the effects of the composition of the present invention.

Immunization for treatment of patients with cellular immune deficiencies associated with cancer, HIV infection, aging, renal transplants and other such deficiencies can be achieved with the composition of the present invention.

The present invention has numerous embodiments. In one embodiment, the present invention provides a method of immunotherapy to treat cancer by administering an effective amount of an NCM including cytokines including, but not limited to, IL-1, IL-2, IL-6, IL-8, IL-12, IFN-δ, TNF-α, GM-CSF, G-CSF, recombinants thereof, and combinations thereof. The above method further includes administering 75 to 500 units IL-2 equivalence, wherein the administering preferably occurs bilaterally into lymphatics that drain into lymph nodes. Alternatively, the administering can occur unilaterally. The NCM is administered for at least one to ten days and up to about twenty days. In one preferred embodiment, administration occurs bilaterally and for about 10 days. The NCM can be administered prior to surgery or radiotherapy. Alternatively, the NCM can be administered during recurrence of tumors. In addition to the NCM, an effective amount of CY can be administered. Furthermore, an effective amount of an NSAID can be administered wherein the NSAID can be, but is not limited to, INDO, Ibuprofen, celecoxib (Celebrex®), rofecoxib (Vioxx®), CoxII inhibitors, combinations thereof, and any other similar NSAID known to those of skill in the art.

In another embodiment of the present invention, there is provided a method of immunotherapy to treat cancer by administering an effective amount of CY and an effective amount of INDO. Another embodiment of the present invention provides a synergistic anti-cancer treatment method by administering an effective amount of a CY and an effective amount of a NSAID, wherein the NSAID can be, but is not limited to, INDO, Ibuprofen, celecoxib (Celebrex®), rofecoxib (Vioxx®), CoxII inhibitors, combinations thereof, and the like.

Another embodiment of the present invention provides a method of immunotherapy to treat cancer by administering an effective amount of CY in combination with an effective amount of INDO and an effective amount of IFN-δ, IL-2, IL-1, and TNF-α. A further embodiment is directed towards a method of immunotherapy to treat cancer by administering an effective amount of CY in combination with an effective amount of INDO and an effective amount of recombinant IL-2, recombinant IFN-δ, recombinant TFN-α, and recombinant IL-1.

A synergistic anti-cancer treatment is also provided by the present invention, wherein the treatment includes the steps of administering an effective amount of CY and INDO in combination with a NCM. The NCM can include, but is not limited to, IL-1, IL-2, IL-6, IL-8, IL-12, IFN-δ, TNF-α, GM-CSF, G-CSF, recombinants thereof, combinations thereof, and any other similar cytokine known to those of skill in the art.

An anti-metastatic treatment method is another embodiment of the present invention wherein the method includes the steps of promoting differentiation and maturation of immature dendritic cells in a lymph node, allowing presentation by resulting mature dendritic cells of antigen to T-cells to gain immunization of the T-cells to the antigen, and preventing development of metastasis.

A further embodiment provides for an anti-metastatic method including the steps of unblocking immunization at a lymph node, and generating systemic immunity. This method further includes the step of preventing development of metastasis.

Other embodiments of the present invention provide a method of using a natural cytokine mixture as a diagnostic skin test for predicting treatment outcome by administering an NCM intracutaneously and determining a response to the NCM within 24 hours, wherein a negative skin test indicates unresponsiveness to the NCM and predicts failure of patients to respond to surgery with or without radiotherapy. Another embodiment provides a method of pre-treatment of dendritic cells (DC) by applying an effective amount of CY and INDO in combination with an NCM including cytokines such as, but not limited to, IL-1, IL-2, IL-6, IL-8, IL-12, IFN-$\delta$, TNF-$\alpha$, GM-CSF, G-CSF, recombinants thereof, combinations thereof, and any other similar cytokines known to those of skill in the art.

The present invention provides a method of treating monocyte defects characterized by sinus histiocytosis or a negative NCM skin test by applying an effective amount of CY and INDO in combination, with an NCM. The NCM includes, but is not limited to, IL-1, IL-2, IL-6, IL-8, IL-12, IFN-$\delta$, TNF-$\alpha$, GM-CSF, G-CSF, recombinants thereof, combinations thereof, and any other similar cytokines known to those of skill in the art.

Further, the present invention provides various methods of eliciting an immune response to endogenous or exogenous tumor antigens by administering an effective amount of an NCM that includes various cytokines including, but not limited to, IL-1, IL-2, IL-6, IL-8, IL-12, IFN-$\delta$, TNF-$\alpha$, GM-CSF, G-CSF, recombinants thereof, or combinations thereof. Another embodiment of the present invention provides administering the NCM described above and an effective amount of CY to elicit an immune response to endogenous or exogenous tumor antigens. In yet another embodiment of the present invention, the method of eliciting an immune response to endogenous or exogenous tumor antigens occurs by administering an effective amount of an NCM; an effective amount of CY; and an effective amount of INDO, wherein the NCM includes cytokines such as, but not limited to, IL-1, IL-2, IL-6, IL-8, IL-12, IFN-$\delta$, TNF-$\alpha$, GM-CSF, G-CSF, recombinants thereof, and combinations thereof.

The present invention also provides a composition for eliciting an immune response to endogenous or exogenous tumor antigens. The composition includes an effective amount of NCM, wherein the NCM includes cytokines such as, but not limited to, IL-1, IL-2, IL-6, IL-8, IL-12, IFN-$\delta$, TNF-$\alpha$, GM-CSF, G-CSF, recombinants thereof, and combinations thereof. In a further embodiment, the composition includes an effective amount of CY. In yet another embodiment, the composition further includes an effective amount of INDO.

For any of the above embodiments, the following administration details and/or protocols for treatment are used.
Administration and Protocols for Treatment:
Delivery of Gene Products/Synthetic Antigens:

The compounds of the present invention (including NCM), and exogenous antigens are administered and dosed to achieve optimal immunization, taking into account the clinical condition of the individual patient, the site and method of administration, scheduling of administration, patient age, sex, body weight. The pharmaceutically "effective amount" for purposes herein is thus determined by such considerations as are known in the art. The amount must be effective to achieve immunization including but not limited to improved tumor reduction, fragmentation and infiltration, survival rate or more rapid recovery, or improvement or elimination of symptoms.

In the method of the present invention, the compounds of the present invention can be administered in various ways. It should be noted that they can be administered as the compound or as pharmaceutically acceptable salt and can be administered alone or as an active ingredient in combination with pharmaceutically acceptable carriers, diluents, adjuvants and vehicles. The compounds can be administered intra or subcutaneously, or peri or intralymphatically, intranodally or intrasplenically or intramuscularly, intraperitoneally, and intrathorasically. Implants of the compounds can also be useful. The patient being treated is a warm-blooded animal and, in particular, mammals including man. The pharmaceutically acceptable carriers, diluents, adjuvants and vehicles as well as implant carriers generally refer to inert, nontoxic solid or liquid fillers, diluents or encapsulating material not reacting with the active ingredients of the invention.

The doses can be single doses or multiple doses over a period of several days. When administering the compound of the present invention, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Peptides can be polymerized or conjugated to carriers such as human serum albumen as is well known in the art. Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The foregoing provides a protocol for using NCM as an adjuvant to immunize cancer patients against tumor antigens, either autologous or as defined proteins or peptides.

| The antigen preparations to be used: | In Cancer: |
|---|---|
| 1) PSMA peptides (9)-obtained commercially | Prostate |
| 2) MAGE 1 & 3 & MAGE fragments & NY ESO-1 obtained from the Ludwig Inst. Of Immunol. | Melanoma, H&NSCC |
| 3) Papilloma virus E6 & E7 obtained commercially | Cervical SCC |

The commercially route of antigen administration is preferentially the neck because it is accessible and it contains >30% of the bodies lymph nodes and systemic immunity can be envisioned to result.

Low Dose CY:

Low dose CY has been used to augment cellular immunity and decrease suppression by lymphocytes in mice and patients with cancer (Berd D., Progress in Clin Biol Res 288:449–458, 1989; Berd D, et al, Cancer Research 47:3317–3321, 1987) and it has been employed in effective immunotherapy of cancer patients (Weber J., Medscape Anthology 3:2, 2000; Murphy G P, Tjoa B A, Simmons S J. The prostate. 38:43–78, 1999; Hadden J W, et al, Arch Otolaryngol Head Neck Surg. 120:395–403,1994).

Zinc:

Zinc deficiency is associated with improved cellular immunity and treatment with zinc is immunorestorative in mice (Hadden J W., Int'l J Immunopharmacol 17:696–701, 1995; Saha A., et al. Int'l J Immunopharmacol 17:729–734, 1995).

A Cyclooxygenase Inhibitor (COXi) Such as INDO:

Cancers produce prostaglandins and induce host macrophage production of prostaglandins (Hadden J W. The immunopharmacology of head and neck cancer: An update. Int'l J Immunopharmacol 11/12:629–644,1997). Since prostaglandins are known to be immunosuppressive for T cells, inhibition of PG synthesis with cyclooxygenase inhibitors is appropriate.

Recombinant Protein Purification:

Marshak et al, "Strategies for Protein Purification and Characterization. A laboratory course manual." CSHL Press, 1996.

Dose and Frequency of Antigens:

1–1000 µg, preferably 10–500; form-soluble (partially polymerized or conjugated to carrier, if necessary). Dosage administration occurs on Day 1, Day 12, and Day 21. Pre-Rx occurs on Day 12, Day 21, and Day 31. Site of injections is local (i.e., neck injections).

Expected Responses:

1) Tumor reduction;
2) Tumor pathological changes (reduction, fragmentation, lymphoid infiltration);
3) Humoral immunity to antigen (RAI or ELISA); and/or
4) Cellular immunity to antigen (intracutaneous skin test in vitro lymphocyte proliferation, of ELISPOT ASSAY).

Oligopeptides such as PSMA, MAGE fragments, E6, E7 peptides would be poorly immunogenic even pulsing on to dendritic cells. Thus effective immunization would not be expected to occur. Even with effective immunization, tumor regression would be considered surprising by this method, particularly at a distance as with prostate and cervix. Regression of metastastic disease is always a surprising event with immunotherapy. Degree and frequency of clinical responses are a factor in the effectiveness and thus the novelty of this approach.

Diagnostic skin tests are another way towards obtaining more effective immunization. Patients can be pretreated with the NCM of the present invention to induce better responses (increase NCM and PHA skin tests and lymphocyte counts and reversal of lymph node abnormalities). As a result, an adjuvant strategy has been created, wherein combining immunorestoration and adjuvancy occurs, making peptides and proteins immunogenic takes place, and getting the degree of immune response to effect tumor regression at a distance is possible.

Patients can be skin tested for one or more tumor peptide prior to consideration of the protocol, 100 pg of one or more tumor peptides can be perilymphatically administered in the neck with NCM using the NCM protocol as discussed below on day 1 and 10 of the NCM series. The combination will be repeated on day 21. In addition to tumor response and histology, immune reaction to the peptides will be monitored by repeat skin test or by other means known in the art.

The above discussion provides a factual basis for the use of the present invention. The methods used with a utility of the present invention can be shown by the following non-limiting examples and accompanying figures.

EXAMPLES

Materials and Methods:

All steps relating to cell culture are performed under sterile conditions. General methods of cellular immunology not described herein are performed as described in general references for Cellular immunology techniques such as Mishell and Shiigi (Selected Methods in Cellular Immunology, 1981) and are well known to those of skill in the art.

Preparation of Natural Cytokine Mixture (NCM):

The buffy coat white cells of human blood from multiple HIV-negative hepatitis virus-negative donors is collected. In an alternative embodiment, animals could be the cell source for veterinary uses. The cells from the donors are pooled and layered on ficoll hypaque gradients (Pharmacia) to yield lymphocytes free of neutrophils and erythrocytes. Alternative methods could be used that would result in the same starting lymphocyte population as are known in the art.

The lymphocytes are washed and distributed in X vivo-10 media (Whittaker Bioproducts) to surface activated cell culture flasks for selection of cell subsets MICROCELLECTOR™ T-25 Cell Culture Flasks) in which are immobilized stimulants, i.e. mitogens like PHA. In one set of experiments, X vivo-15 and X vivo-20 media were used as indicated. The immobilization process for the stimulants is as described by the manufacturer for immobilizing various substances for panning procedures, i.e. separating cells, in the flasks. Alternatively, the lymphocytes are exposed to stimulants e.g. PHA for 2–4 hours then washed three times.

The cells are incubated for 24–48 hours in X vivo-10 media with 80 µg/ml ciprofloxacin (Miles Lab) at 370 in a $CO_2$/air incubator. Alternatively, RPMI 1640 media could be used (Webb et al. 1973). Generally the HSA is used at 0.1 to 0.5% (weight by volume). Following incubation the supernatants are poured off and collected. Human serum albumin (HSA) may be added to stabilize further the interleukins if HSA-free media is used for generations. The supernatants are stored at 4° C. to −70° C.

Stimulation of Lymphocytes:

The objective was to find a way to stimulate lymphocytes to produce high levels of interleukin-2 in the absence of serum and in a way that did not yield significant quantities of PHA in the supernatant. To do this, the PHA was immobilized on surface activated cell culture flasks for selection of cell subsets (AIS MICROCELLECTOR™ T-25 plates) as described in the manufacturer's instructions for "panning" cell separation or pulsed into the cells followed by washing (pulse technique).

Media employed in these experiments was X vivo-10 (Whittaker) and is approved for administration to humans by the U.S. Food and Drug Administration for interleukin-2 lymphokine activated killer (LAK) cell protocols. Serum-free media capable of supporting human lymphocyte proliferation like minimal essential media (MEM) or RPMI-1640 (Sigma) could also be used.

Initial experiments indicated that PHA (HA-16, Murex Diagnostics Ltd., Dartford, UK) could be immobilized by the technique described by the manufacturer and that under appropriate optimal conditions of cell number of $7.5–15 \times 10^6$/ml, time of exposure of 24 hours to 48 hours, and PHA concentration of 25 or 50 μg/ml a high yield of IL-2 in the serum-free supernatant could be obtained. Additional detailed information is set forth in International Publication Number WO 03/035004 A2 to Hadden and International Publication Number WO 02/34119 A2 to Hadden, which are incorporated herein by reference in their entirety.

Preparation of NCM:

For the examples described herein, pooled human peripheral blood buffy coats obtained from INCAN Blood Bank were incubated with phytohemagglutinin (Murex, Dartford UK) and washed. The cells were incubated in serum-free medium (x-vivo 10, BioWhitaker) for twenty four hours. Batches were prepared from six blood donors and were screened by the INCAN Blood Bank for hepatitis B and C viruses, HTLV 1 and 2, and HIV. Following twenty-four hours of culture, the cultures were centrifuged, the supernatant was filtered through 0.2-micron filters, and the natural cytokine mixture was placed into vials. Activity of the batches of NCM of the present invention averaged 200 U/ml of IL-2 as determined by ELISA. Vials of the batches were stored at −70° until use.

Cytokines were assayed using commercial ELISA kits (Quantikine™, R & D Systems, Inc., Minneapolis, Minn.) (See, Table I). Biological activity of the NCM of the present invention was confirmed using a murine cytotoxic T-cell line (CTLL-2), which was originally developed as an indicator of biological activity of IL-2.

TABLE I

NCM cytokine contents for five lots used at INCAN

| Lot No. Designations: | IL-2 Activity IU/mL | IL-1β pg/Ml | Il-2 pg/mL | IFN-γ pg/mL |
|---|---|---|---|---|
| 1 | 188 | 439 | 7228 | 1802 |
| 2 | 189 | 444 | 7253 | 1854 |
| 3 | 197 | 427 | 7575 | NT |
| 4 | 168 | 370 | 6449 | 1929 |
| 5 | 171 | 449 | 6576 | 2527 |
| Mean | 183 | 426 | 7016 | 2028 |
| S.D. | 12 | 32 | 482 | 337 |

Patients:

Forty-two patients with Stage I–IV squamous cell carcinomas of the head and neck entered the trial (Hadden, et al., International Immunopharmacology 3; 1073–1081 (2003)). Twenty-seven patients were treated with one or more 10-day courses of the NCM of the present invention. Fifteen patients received a 20-day course of the NCM of the present invention at two neck sites. Four of these patients received a preparation of the NCM of the present invention that had low levels of cytokines (1/4x, wherein these patients were excluded from statistical analysis). Ten other patients did not meet study inclusion criteria at the time of the study entry, but were treated with the NCM in a compassionate manner. Compassionate treatment occurred because of a response to a negative skin test to NCM, occurrence of metastatic disease, or not being a surgical candidate. The median age of all patients was 66.0 years (range 34–86) and the male:female ratio was 4:1. The majority of patients had Stage III & IV squamous cell carcinomas of the larynx or the oral cavity. Stage I & II patients had tongue lesions.

Response was estimated based on standard oncology criteria and tumor. Survival was estimated by the Kaplan-Meier plots using a computer software statistics package (GRAPHPAD™, San Diego, Calif.) where complete response (CR), partial response (PR) of greater than 50% tumor reduction, and no response or less than 25% tumor reduction was recorded.

Treatment Regimen:

Each treatment cycle lasted twenty-one days. Each cycle was initiated with an intravenous infusion of cyclophosphamide (CY) at 300 mg/m$^2$ and indomethacin (INDO) at 25 mg orally three times a day, and zinc (65 mg elemental zinc as the sulfate) orally once a day. Patients also underwent skin-testing with NCM at 0.1 mL administered intradermally to rule out allergic response to components and to show delayed type hypersensitivity (DTH) responses to NCM on day 4. Patients were treated with the NCM at 1.0 mL for ten days or 2.0 mL for twenty days administered intramuscularly at the insertion of the sternocleidomastoid muscle 2.0 cm below the mastoid tip. In those patients who had undergone surgery, treatment was administered in the intact neck contralateral to the side of the surgery. All patients gave signed informed consent to participate in the study and the study was approved by the Institutional Review Board and the Research Committee of INCAN as well as the Mexican Ministry of Health. Patients with any underlying immunological disorders, severe systemic disease, or patients requiring immunosuppressive therapy were excluded from the trial. Patients who were surgical candidates were taken to surgery on Day 21; post-operative radiation therapy was administered for patients who were at high risk of recurrence (e.g., those with involved nodes and/or positive surgical margins) at the discretion of the surgeon and consulting radiation oncologist. Routine surgical pathology was performed on all pre- and post-treatment biopsy specimens. To quantify the various histological components of the tumor, a representative biopsy section containing a tumor was selected under low power and the amount of tumor was expressed as a percent of the total area. The remaining stroma was evaluated for the percent of the area having lymphocytes. Tumors were further evaluated for the percent of the specimen area that was solid and the percent fragmented with interspersed leukocyte as infiltration as described.

TABLE II

| Patient Characteristics of study in head & neck cancer ||
|---|---|
| Number of Patients | 42 |
| Median Age (range) | 65.0 (34–91) |
| M:F Ratio | 32:8 |
| Median KPS (range) | 100 (70–100) |
| Treatment Regimen | |
| 10 days | 20 |
| 20 days | 22 |
| Compassionate use | 7 |
| Low dose | 4 |
| Primary Tumor | |
| Larynx | 15 |
| Tongue | 8 |
| Gingiva | 5 |

TABLE II-continued

Patient Characteristics of study in head & neck cancer

| Sinus | 3 |
| Tonsil | 3 |
| Floor of Mouth | 1 |
| Retromolar trigone | 2 |
| Buccal mucosa | 2 |
| Lip | 1 |
| External ear | 1 |
| Unknown primary | 1 |
| Stage at Diagnosis | |
| I | 1 |
| II | 6 |
| III | 12 |
| IV | 23 |

Example 1

Local perilymphatic injections in the neck having NCM plus low dose CY, INDO, and zinc have induced clinical regressions in a high percentage of patients with squamous cell head and neck cancer (H&NSCC) (Hadden J W, et al., Arch Otolaryngol Head Neck Surg. 120:395–403,1994; Meneses A, et al., Arch Pathol Lab Med 122:447–454, 1998; Barrera J, et al., Arch Otolaryngol Head Neck Surg 126:345–351, 2000; Hadden, et al., 2003; Menesis, et al., 2003) with evidence of improved, recurrence-free survival. Overall, including minor response (25%–50%) tumor shrinkage and reduction of tumor in pathological specimens, over 90% responded and the majority had greater than 50% tumor reduction.

These responses are speculated to be mediated by immune regression since both B and T lymphocytes were observed infiltrating the tumors. The therapy was not associated with significant toxicity. Treatment of lymphocytopenic cancer patients with the combination of NCM has resulted in marked lymphocyte mobilization; where analyzed, these patients showed increases in CD45RA positive T-cells (i.e., naive T cells (Table IV)). Further, intratumoral or peritumoral injection of NCM in patients with H&NSCC resulted in either reversing immunotherapy-induced tumor regression or in progression of the tumor. The tumor is thus not the site of immunization. As a result, analysis of regional lymph nodes revealed data that indicates that the regional lymph node is the site of immunization to postulated tumor antigens (Meneses, et al., 2003)(See, FIGS. 1–5). None of these patients treated with NCM developed metastasis expected in 15% clinically and up to 50% pathologically, indicating systemic immunity rather than merely local immunity had been induced. Patients were pretested with a skin test to 0.1 ml of NCM prior to treatment and more than 90% of those with a positive skin test (>0.3mm at 24 hours) had robust clinical and pathological response. Patients with negative skin tests had weak or no response. Thus, skin testing selects good responders.

Major increases were observed in T lymphocyte counts (CD2) 752→1020 in these T lymphocytopoenic patients (T cell counts 752 vs. 1600(normal)). Importantly, there was a corresponding increase in "naive" CD45RA positive T cells (532→782). As previously mentioned, these increases are generally not thought to occur in adults particularly with a pharmacological therapy like NCM. These cells presumably are recent thymic emigres and could be considered a major new capacity for responding to new antigens like tumor antigens. The preexisting CD45RA positive cells were not responding to the tumor antigens and can be incapable of doing so due to the tumor-induced immune suppression (anergy).

The literature (Hadden J W, Int'l J Immunopharmacol 11/12:629–644, 1997; Hadden J W, Int'l J Immunopharmacol 21:79–101, 1999) indicates that for both SCC and adenocarcinomas, the two major types of cancer, regional lymph nodes reflect abnormalities related to the tumor, including sinus histocytosis, lymphoid depletion and often the presence of tumor-associated lymphocytes capable of reacting to tumor cells (with IL-2). With metastasis, lymphoid depletion and depressed function occur. An unpublished analysis of uninvolved cervical lymph nodes 10 H&NSCC and 10 controls showed reduction in average size and an increase in sinus histocytosis associated with H&NSCC (FIGS. 1–4).

TABLE III

Treatment of Lymphocytopoenic Patients with H&NSCC with NCM-Increases in Naïve T Cells in Blood (#/mm)

| PATIENT # | NAÏVE T CELL MARKER | | | PAN T CELL MARKER | | |
| --- | --- | --- | --- | --- | --- | --- |
| | PRE | POST | INCREASE | PRE | POST | INCREASE |
| 1 | 479 | 778 | +299 | 704 | 1171 | +467 |
| 2 | 938 | 1309 | +371 | 1364 | 1249 | −115 |
| 3 | 98 | 139 | +41 | 146 | 178 | +32 |
| 4 | 341 | 438 | +97 | 655 | 590 | −65 |
| 5 | 567 | 652 | +97 | 453 | 643 | +190 |
| 6 | 658 | 1058 | +400 | 1118 | 1714 | +569 |
| 7 | 642 | 1101 | +459 | 822 | 1601 | +779 |
| MEAN | 532 | 782 | +250 | 752 | 1020 | +269 |

Following treatment with one cycle of the NCM protocol (Hadden J W, et al., Arch Otolaryngol Head Neck Surg. 120:395–403, 1994; Meneses A, et al., Arch Pathol Lab Med 122:447–454, 1998; Barrera J, et al., Arch Otolaryngol Head Neck Surg 126:345–351, 2000), the uninvolved cervical lymph nodes showed the changes indicated in FIGS. 1–4). Compared to the regional lymph nodes of patients with H&NSCC not treated with NCM, these nodes showed a significant increase in size, T cell area and density, and decreases in number of germinal centers and sinus histocytosis and congestion. The lymph nodes of treated patients were all stimulated and were larger than control nodes with increased T cell area and density. These nodes were thus not only restored to normal but showed evidence of T cell predominance, a known positive correlate with survival in H&NSCC (Hadden J W. Int'l J Immunopharmacol 11/12:629–644,1997).

Figure 5:
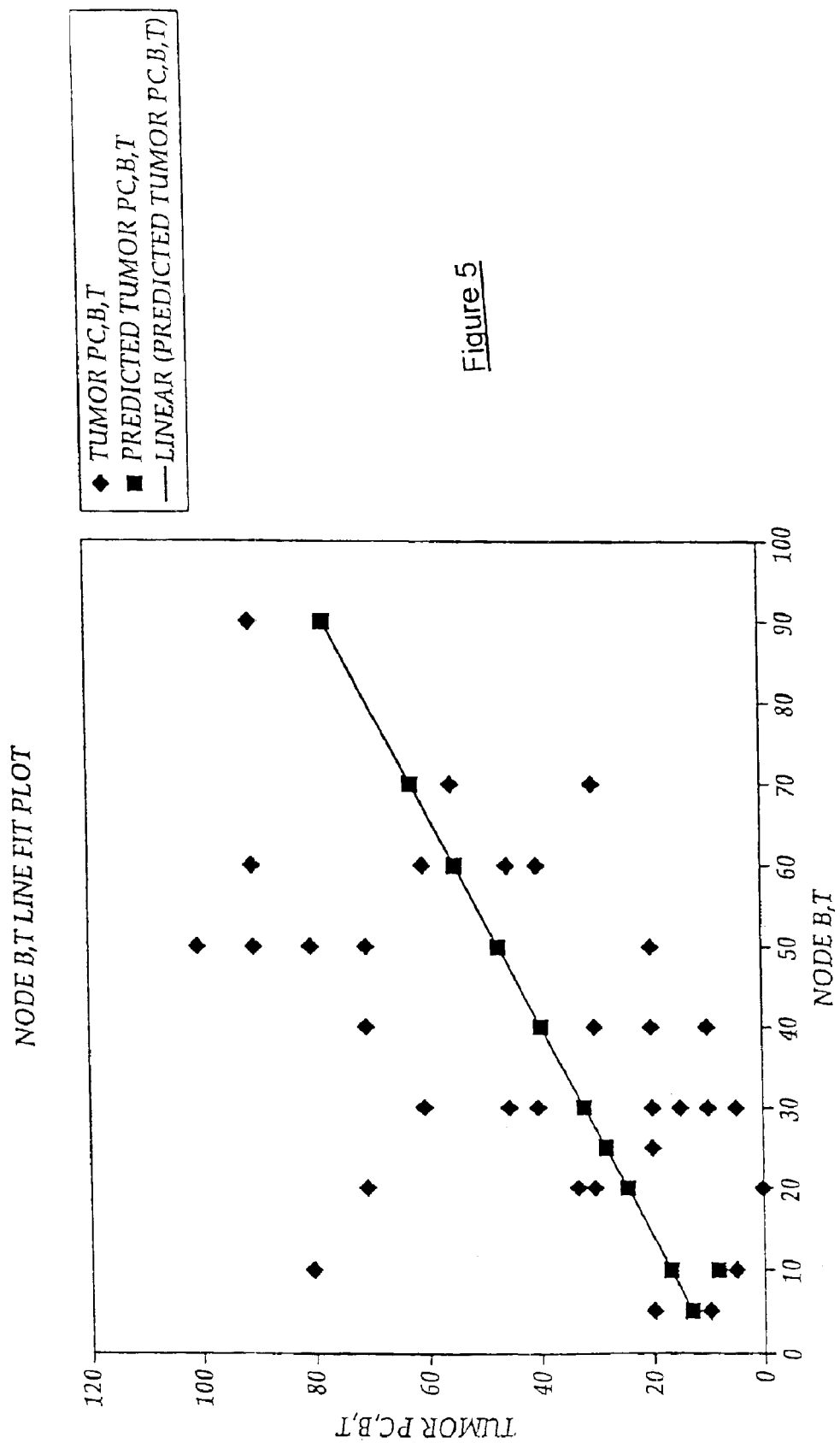
FIG. 5 is a graph showing node B&T and Cancer B&T fit plot.

Importantly, when the lymph node changes related to B and T cell areas were correlated with the changes in their tumors reflecting T and B cell infiltration, a high degree of correlation was obtained for T cells (p.<0.01) and B cells (<0.01) and overall lymphoid presence (p.<0.001)(FIG. 5). In turn, these changes correlate with tumor reduction by pathological and clinical criteria. These findings indicate that the tumor reactions are directly and positively correlated with lymph node changes and that the tumor reaction reflects the lymph node changes as the dependent variable. These findings, taken into conjunction with knowledge about how the immune system works in general (Roitt I, Brostoff J, Male D. Immunology, J B Lippincoft Co, Phila, Pa., 1989), and following tumor transfection with a cytokine gene (Maass G, et al, Proc Natl Acad Sci USA, 1995, 92:5540–5542), indicate that the NCM protocol immunizes these patients to yet unidentified tumor antigens at the level of the lymph nodes. No one has previously presented evidence for lymph node changes reflecting immunization with autologous tumor antigens. This confirms that the present invention can induce immunization with previously ineffective or poorly effective tumor antigens in an effect to yield regression of distant metastases.

Example 2

Figure 6:
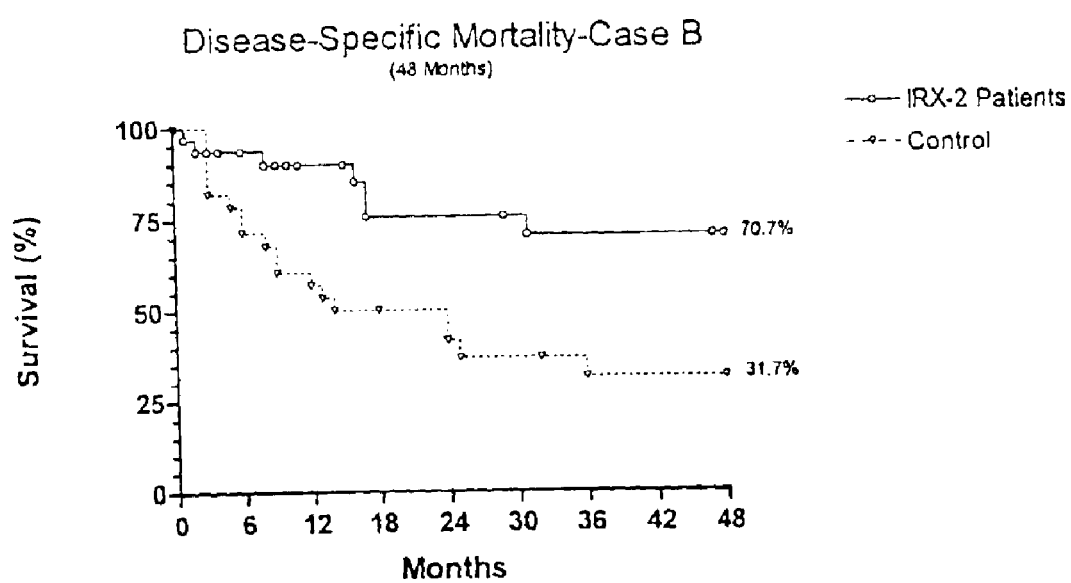
FIG. 6 is a graph illustrating the survival percentage of treated patients at forty-eight months.
Figure 7:
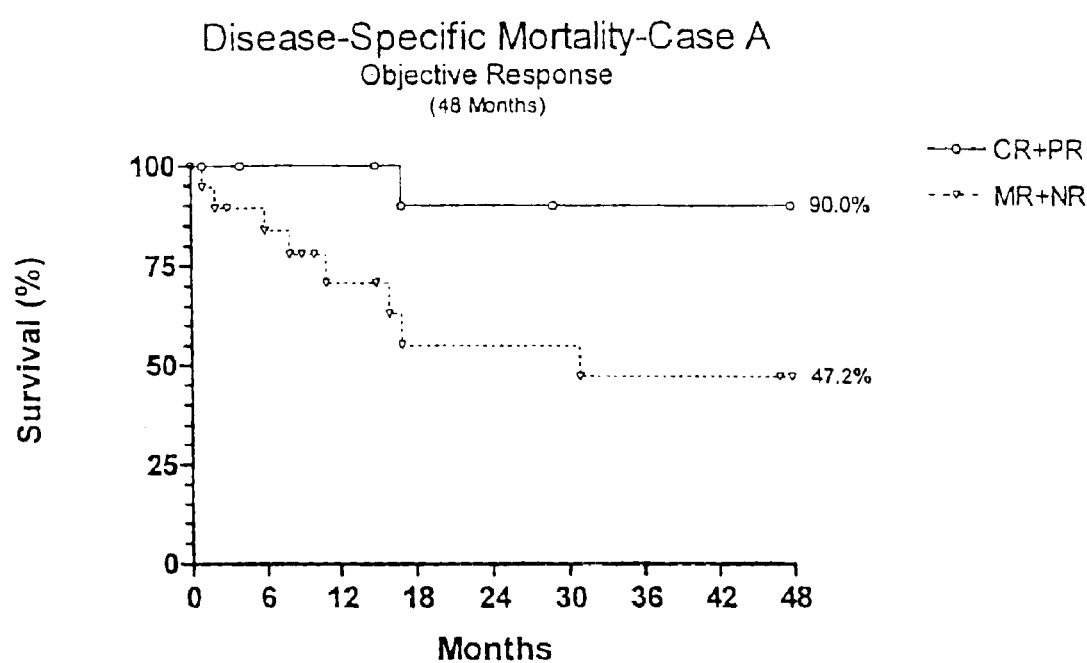
FIG. 7 is a graph illustrating the survival of complete and partial responders compared to minor and non-responders.
Figure 8:
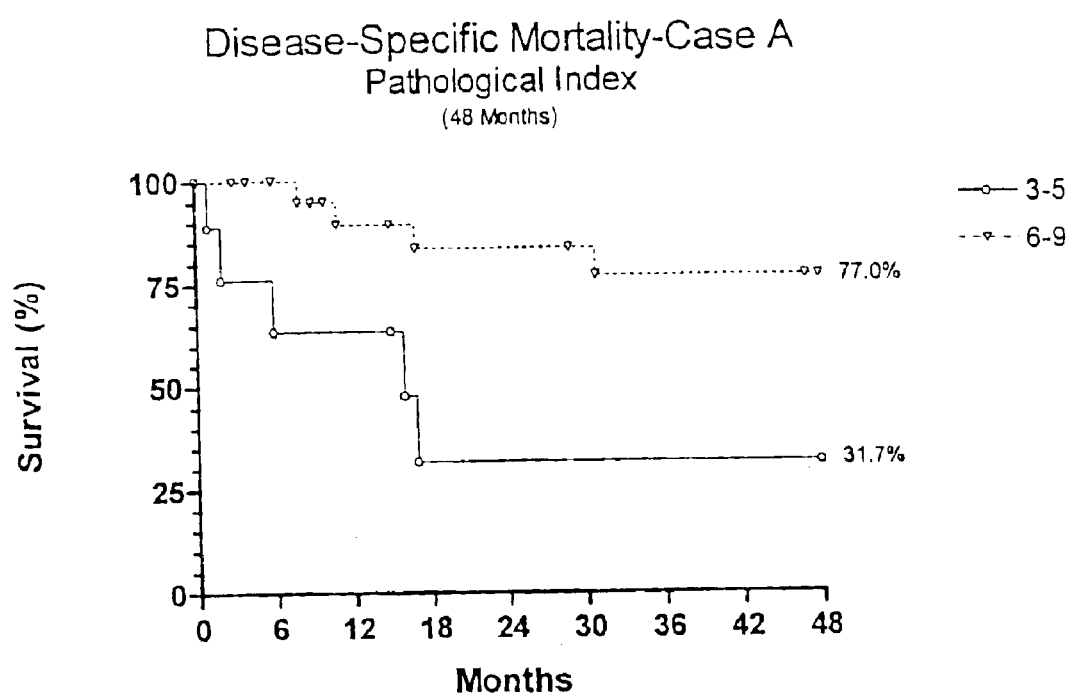
FIG. 8 is graph illustrating the relation of the pathology index to survival.
Figure 9:
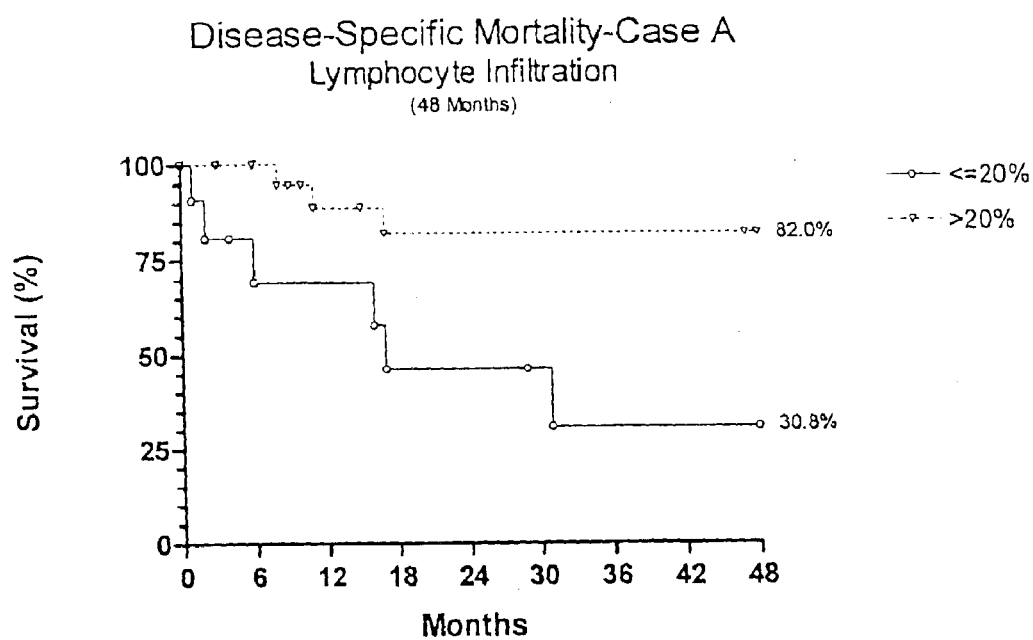
FIG. 9 is a graph showing the relationship of lymphocyte infiltration to survival.

Further analysis of the clinical, pathological and survival data of the aforementioned INCAN study offer more insights into the nature of the invention as it relates to immunization of cancer patients to their own autologous tumor antigens and the resulting immune regression of their tumors. FIG. 6 shows that the treatment with the NCM protocol (IRX-2) is associated with increased survival at 48 months (p<0.01). FIG. 7 shows that clinical responses determine survival in that patients with complete (CR) and partial responses (PR)(>50% tumor reduction) have better survival than those with minor responses (MR) (<50%, but >25% tumor reduction) or no response (NR)(<25%)(p<0.01). FIG. 8 shows that patients with stronger pathological responses (index of 6–9) have better than those with weaker pathological responses (<6) (p<0.02). FIG. 9 shows that lymphoid infiltration into the tumor as a single variable predicts survival (p<0.01). Finally, Chi Square analysis of the relationship of clinical response to the pathological response shows a highly significant relationship (p<0.01) indicating that the two are coordinately related to each other as well as to survival and thus providing a statistical triangulation of the data interrelating clinical responses, immune regression parameters, and survival. Such relationships have never been shown for immunotherapy of a human cancer.

Example 3

Two patients were treated with lymphoma of the head and neck. The patients included were those with head and neck cancer who agreed to participate in the protocol. The following scheme was followed.

Before treatment, the patients were skin-tested with NCM 0.1 ml subcutaneously in the forearm, the region was marked, and 24 hours later the test was read. The test was considered positive if the induction and erythema was equal or larger than 3mm.

Case 1:

The patient was a 23-year-old male who presented on with a prior history of three months of the presence of a tumor on the left submaxillary region, with no other symptoms. In the emergency room, he was found to have lymph adenopathy of the left submaxillary triangle of approximately 6.5 cm in diameter of a hard consistency, partially fixed at deep levels. The rest of the physical exam was normal. The incisional biopsy showed Hodgkin's lymphoma. The lesion was staged ECIIA. A one-cycle treatment of NCM was given, obtaining a minor response, as the adenopathy reduced in size by 1 cm in diameter. The biopsy report obtained after NCM treatment showed 60% of the lesion showed normal lymphocytic infiltration, and the rest of the neoplasia (40%) showed necrosis. No viable tumor cells were found.

Following this, the patient received radiation treatment in the neck of 3600 rads. The patient is currently free of disease.

Case 2:

The patient is an 82-year-old male, who presented with a two-month history of a painful mid-neck tumor mass, as well as a 10 kg loss of weight. On physical exam, the patient presented with tumor on the right palatine tonsil, which was enlarged to approximately 4×3 cm, with an ulcer in the center of the tonsil. On the neck, a right submaxillary lymph node measured approximately 2×2 cm and a lymph node mass at level II and III of approximately 5×5 cm. The rest of the exam was normal. The incisional biopsy of the tonsil and one of the neck's lymph nodes demonstrated defined non-Hodgkin's lymphoma mixed, of intermediate grade.

The patient was subjected to two cycles of NCM at the end of which a 1 cm reduction in the diameter of the tonsil and neck adenopathy was observed. The pathological report post-NCM treatment showed live tumor 20%, fragmented and necrotic 30% and normal lymphocyte infiltration 50%.

The patient was given chemotherapy (CHOP) for 6 cycles and later external radiotherapy (RT) at a total dose of 4600 rads. He recurred at eight months post RT with adenomegaly at the occipital level. The patient died three months later with evidence of neck disease.

Example 4

Ten patients with untreated early stage cervical cancer, clinically staged IB1, IB2 and IIA were treated with local, perilymphatic injections NCM (10 daily injections) followed by radical hysterectomy at day 21. One day before starting the NCM treatment of the present invention, patients received a single IV dose of CY at 300 mg/m. oral INDO or ibuprofen and zinc sulfate were administered from days 1 to 21. The clinical and pathological response, toxicity and disease-free survival were evaluated.

All patients completed NCM treatment and were evaluated for response and toxicity. Clinical response was seen in 50% of patients (3 partial response (PR), 2 minor response (MR) (>25%<50% reduction)). Seven patients underwent surgery. Pathologically tumor reduction associated with tumor fragmentation was found in five cases. There was a rather heterogeneous pattern of cell types infiltrating the tumor, which included lymphocytes, plasma cells, neutrophils, macrophages and eosinophils. Treatment was well-tolerated except for mild pain and minor bleeding during injection and gastric intolerance to INDO. At 24-months of follow-up, nine patients were disease-free.

This previously unpublished study shows that peritumoral NCM induces immune-mediated tumor response in early stage untreated cervical carcinoma.

Example 5

Two patients with liver metastasis from primary hepatocellular carcinoma were treated with intrasplenic NCM (1 or 3 injections). The protocol was otherwise as previously described for the H&NSCC, cervical, or lymphoma cases. One patient with advanced hepatocellular carcinoma had a partial response confirmed by tomography, no histology is available. The other had a partial response confirmed by surgery. Histological exam showed tumor reduction, fragmentation, and lymphoid infiltration.

Example 6

Four patients with squamous cell carcinoma of the penis (human papiloma virus associated) were treated with the NCM protocol as described above; all four had partial responses clinically and the surgical specimen showed tumor reduction and fragmentation and lymphoid infiltration characteristic of the H&NSCC cancer patients.

Example 7

Dose and Frequency of the Natural Cytokine Mixture:

A ten day injection protocol was compared to twenty day injection protocol. Bilateral injections were compared to unilateral injections and a series of doses were compared. Significant activity on survival was observed from 74–1310 units of IL-2 equivalence (as measured by ELISA, R & D Systems) with a peak at 100–233 units (FIG. 9). Bilateral injections were effective and in one recurrent patient who had undergone an ipsilateral lymph node dissection, contralateral injection was used and a good response was obtained. This observation signifies that tumor antigen may also reside in contralateral nodes and thus bilateral injections are favored. The twenty-day injection protocol was effective in terms of clinical response and survival yet the surgical specimen showed less lymphoid infiltration (17% area) than the ten-day unilateral protocol (34% area) or ten day bilateral protocol (33% area) (p <0.05). Less lymphoid infiltration with equivalent tumor reduction responses signifies that antibody-mediated immune responses are involved, since these responses are considered less effective than lymphocyte-mediated responses (i.e., cytotoxic T-cells) and the twenty-day injection protocol involves more labor and expense, a ten-day bilateral injection protocol with 100 units of IL-2 equivalence or site is deemed optimal.

Figure 10:
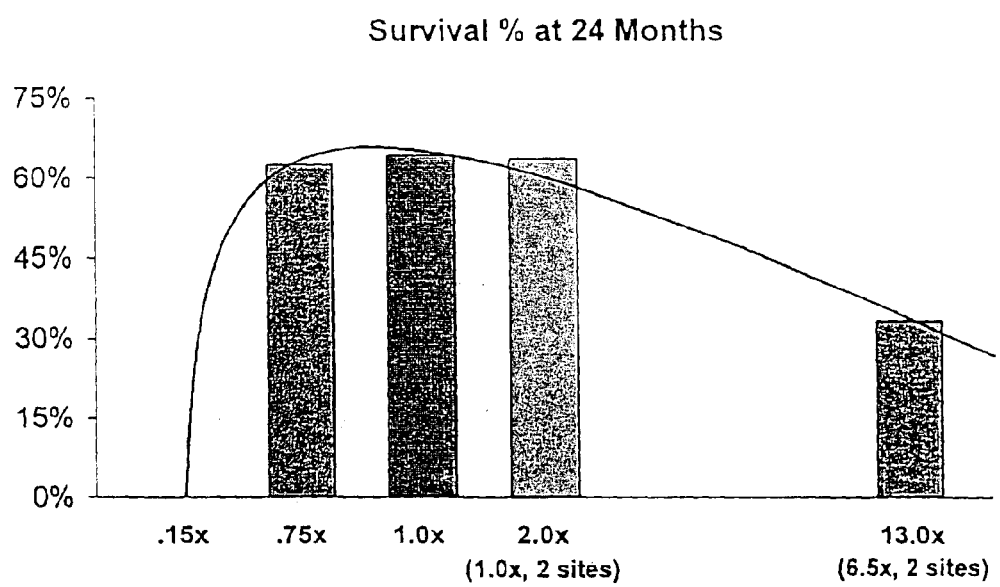
FIG. 10 is a graph illustrating the survival percentage (dose response) of treated patients at twenty-four months, wherein "x" is equal to about 100 IU/mL of IL-2.

FIG. 10 illustrates a series of doses of the NCM of the present invention on overall survival at twenty-four months. An optimal impact on survival at about 100–233 international units of IL-2 equivalence and no effect at about 16 units and less effect at about 1310 units.

Role of the Nonsteroidal Anti Inflammatory Drug (NSAIDs):

INDO is the most potent of NSAIDs acting on both cyclooxygenase I & II, but has greater gastrointestinal (See, Table IV). INDO can increase lymphoid infiltration and tumor reduction in some patients (See, Panje, 1981, and Hirsch, et al., 1983), but it has not been accepted clinically as a useful therapy in H&N SCC. Similarly, CY at this dose is not considered clinically active in H&N SCC. The activity of INDO and CY alone can be considered surprising in the magnitude and type of tumor response. INDO and CY are considered as a synergistic combination for employment with other forms of immunotherapy.

Recently low dose recombinant IL-2 was reported to delay recurrence of metastasis and increase mean survival time in patients with H&N SCC (See, DeStefani, et al., 2002, and Valente, et al, 1990). In the prior art research, no clinical responses were observed and lesser tumor changes (lymphoid infiltration without tumor regression) were observed. Nevertheless, rIL-2 can act with CY & INDO to further induce clinical responses and improve survival. Other natural or recombinant cytokines corresponding to those present in the NCM singly or in combination are also potentially active. For example, cytokines such as IL-1, IFN-$\delta$, TNF-$\alpha$, IL-6, IL-8, GM-CSF, G-CSF, IL-12, and combinations thereof can be used in natural or recombinant form.

TABLE IV

CY & INDO ($\pm$NCM)

| Patient No. | Clinical Response | % Tumor | % Solid | % Fragm | % Stoma | % Lymph | % Tumor Reduction |
|---|---|---|---|---|---|---|---|
| 17 | MR | 20 | 0 | 20 | 0 | 80 | 79 |
| 18 | MR | 60 | 15 | 45 | 0 | 40 | 33 |
| 19 | NR | 45 | 0 | 45 | 15 | 40 | 35 |
| 20 | NR | 70 | 28 | 42 | 15 | 15 | 5 |
| Mean | | 49 $\pm$ 11 | 11 $\pm$ 7 | 38 $\pm$ 6 | 8 $\pm$ 4 | 44 $\pm$ 13 | 38 $\pm$ 15 |

| Patient Population | % Tumor | % Solid | % Fragment | % Stroma | % Lymph | % Tumor Reduction |
|---|---|---|---|---|---|---|
| On-protocol | 48 $\pm$ 5 | 22 $\pm$ 4 | 26 $\pm$ 4 | 19 $\pm$ 5 | 32 $\pm$ 5 | 57 |
| Untreated Controls | 80 | 80 | 0 | 20 | $\pm$ | 0 | toxicity. Newer CoXII inhibitors such as celecoxib (Celebrex®) and rofecoxib (Vioxx®) are thought to have less gastrointestinal toxicity. Use of these two agents in place of INDO in a small series of patients gave lesser responses as measured by clinical and pathological criteria and by survival. In the case of Vioxx®, all seven patients had clinical signs of gastritis following a week of therapy. In the cervical cancer patients, Ibuprofen was used as the NSAID and good responses were obtained. Based upon these observations INDO is preferred, but Celebrex or Ibuprofen can be substituted if INDO is not tolerated. Vioxx® is not recommended. Prilosec or other proton pump inhibitors with or without an oral prostaglandin analog is recommended as prophylaxis for gastritis, while histamine $H_2$ blockers are not considered indicative.

Role of the NSAID in Conjunction With CY:

In four patients a dose of the NCM was given that was considered inactive (See, FIG. 10, 15 units column) in conjunction with INDO and CY. No survivals were observed, yet two patients had minor response (<50%, but >25% tumor shrinkage) and all four showed moderate pathological changes in the tumor specimen with tumor reduction and fragmentation as well as lymphoid infiltration Example 8

Role of the Intradermal Skin Test in Prognosis:

We previously suggested that patients with a negative intradermal skin test to the NCM might show poor clinical responses based upon a single patient. We have now accumulated a series of skin test negative patients and find that they show changes similar to the CY & INDO combination without significant NCM seen in Example 7. Ten patients had negative skin tests (including four from Juarez Hospital) with a NCM of the present invention (i.e., unresponsive to the NCM) and were treated with the NCM plus CY and INDO. These patients had poor clinical responses, smaller tumor reduction and fragmentation, and poor survival (20%) (See, Table V). These observations thus corroborate the conclusion made from Example 7 that INDO and CY have marked activity without NCM. Importantly they confirm that the skin test is critical for predicting the emphatic clinical and pathological responses that relate to improved survival. In addition, a negative skin test predicts the failure of patients to respond to surgery with or without radiotherapy. The NCM skin test can be usefully employed to predict therapeutic outcome in H & N SCC. Previously, skin testing with dinitrochlorobenzene (DNCB) showed prognostic significance in H & N SCC, but due to the cumbersome procedure requiring sensitization, it is not used clinically anymore. The NCM skin test offers a convenient twenty-four hour test.

Interestingly, these patients divided into two groups. In one group, Table VI b, the responses were especially poor with no survivors. In the other group, Table VI a, these patients converted the negative NCM test into a positive following treatment and showed clinical and pathological responses and survival similar to on-protocol patients (See, Table VI B).

One of these patients had a tumor considered inoperable and was shown to convert the negative test to positive and allowed a second treatment to clinically reduce the tumor and by pathological criteria and to allow prolonged survival following surgery (>7 years). This pretreatment of skin test negative patients with NCM can increase response rates. NCM plus thymosin a, can also be predicted to work (See, United States Published Application No. 20030124136). The negative NCM skin test reflects a monocyte defect and treatment with monocyte-active cytokines in natural or recombinant form would be predicted to be useful singly or in combination thereof. These include, but are not limited to, GM-CSF, M-CSF, TFN-δ, IL-1, IL-6, Il-8, IL-12 and others.

TABLE VI

Serum IgG to ALF Peptide

| Dilution NCM | OVA-PSMA NCM | KLH-PSMA-NCM | OVA-PSMA-CpG |
|---|---|---|---|
| 1/200 | 0.929 | 0.692 | 0.241 |
| 1/400 | 0.989 | 0.518 | 0.208 |
| 1/800 | 0.695 | 0.351 | 0.144 |
| 1/1600 | 0.309 | 0.191 | 0.120 |

TABLE VI B

Serum IgG to LLH Peptide

| | | | |
|---|---|---|---|
| 1/200 | 0.950 | 0.720 | 0.277 |
| 1/400 | 1.013 | 0.502 | 0.200 |
| 1/800 | 0.607 | 0.327 | 0.157 |
| 1/1600 | 0.316 | 0.201 | 0.125 |

TABLE V

Negative NCM Skin Test Patients

| Patient No. | Patient Initials | Tumor % | Solid % | Frag. % | Stroma % | Lymph. % | Absolute Tumor Reduction | Subj. Resp. | Status |
|---|---|---|---|---|---|---|---|---|---|
| Negative NCM Skin Test Changed to Positive ||||||||||
| 13 | ANA | 48 | 15 | 33 | 16 | 36 | 42 | PR | Alive >24 Mos. |
| 15 | ICV | 70 | 63 | 7 | 6 | 24 | 5 | MR | Alive >24 Mos. |
| 22 | JMM | 50 | 10 | 40 | 10 | 40 | 30 | PR | Died without Disease 9 Mos. |
| 27 | MVR | 70 | 28 | 42 | 12 | 18 | 10 | PR | Lost to Follow-up |
| | Mean | 60 | 29 | 31 | 11 | 30 | 22 | | |
| | SD | 12 | 24 | 16 | 4 | 10 | 17 | | |
| Negative NCM Skin Test ||||||||||
| 29 | JISM | 80 | 80 | 0 | 10 | 10 | 0 | NR | Died of Disease <1 Year |
| 30 | AGM | 80 | 48 | 32 | 10 | 10 | 0 | NR | Died of Disease <1 Year |
| 35 | NGS* | 70 | 70 | 0 | 0 | 30 | 0 | NR | Died of Disease <1 Year |
| 36 | GCS* | 50 | 15 | 35 | 10 | 40 | 40 | NR | Died of Disease <1 Year |
| 37 | MJBV* | 80 | 16 | 64 | 16 | 4 | 0 | NR | Died of Disease <1 Year |
| 39 | FHV* | 70 | 28 | 42 | 25 | 5 | 0 | NR | Died of Disease <1 Year |
| | Mean | 72 | 43 | 29 | 12 | 17 | 7 | | |
| | SD | 12 | 28 | 25 | 8 | 15 | 16 | | |

*Drawn from JUAREZ Hospital Experience.

TABLE VI C

| Serum IgG to Ovalbumin | | | |
|---|---|---|---|
| 1/500 | 0.920 | 0.269 | 1.050 |
| 1/1500 | 0.632 | 0.185 | 0.955 |
| 1/3000 | 0.457 | 0.146 | 0.813 |
| 1/6000 | 0.259 | 0.104 | 0.537 |

Example 9
Other Predictors of Prognosis for Use of the Present Invention:

Historically there have been few predictors for outcome in H & N SCC, lymphocyte counts, 1gE and 1gA levels or nutrition were suggested and as mentioned, DNCB skin test has been used. For chemotherapy (5 FU & CISPLATINUM) clinical responses occur prior to surgery in the majority of patients, yet mean survival time and overall survival are essentially unaffected. Thus, immune response appears to relate to the ability of surgery with or without radiotherapy to cure or prolong survival in patients with H & N SCC cancer. The data presented in the examples shows that use of the invention delays recurrence of metastasis in those who have residual tumor after surgery and increases survival in a way that relates to the magnitude of the clinical response and the intensity of the immune assault on the tumor as assessed by quantitation of tumor reduction, fragmentation and lymphoid infiltration. These observations point to important modifications of the invention to further improve survival.

In Patients With Severe Immunodeficiency:

In patients with low lymphocyte counts, weak or absent NCM skin tests, sinus histiocytosis, poor pathological responses, retreatment and monitoring of immune responses would be indicated.

In Patients With Minor or No Clinical Responses:

These patients have a high risk of recurrence of metastasis and thus would logically benefit from post surgical treatment with the NCM of the present invention. In the absence of currently available tests for specific reactivity to the tumor rejection response observed in the patients, follow up testing with the triad of tests described in U.S. Pat. No. 6,482,389 would help to determine the frequency of retreatment with the NCM of the present invention.

In Patients who Recur:

Significant responses were observed including two complete responses in patients who were re-treated with the NCM of the present invention. This is in contrast to previous results with natural and recombinant IL-2 who failed to respond to retreatment. Thus, the present invention is useful for treating recurrence of metastasis in patients.

Example 10
Use of the Invention With Other Treatments Like Radiotherapy or Chemotherapy:

Patients with Stage IV H&N SCC cancers have markedly reduced survival compared to patients with Stage III disease (10–20% vs. 30–50%) despite the addition of radiotherapy. Radiotherapy is well known to depress T lymphocyte counts in these patients for a prolonged period. Despite the negative impact of radiotherapy on T-cell number and function, patients treated with NCM of the present invention having Stage IV disease did as well as patients with Stage III disease. Thus, the therapeutic impact was relatively greater in Stage IV patients, which contradicts current dogma that immunotherapy and cytokine therapy works better with minimal tumor. It also suggests that the invention potentiates the effect of radiotherapy. Similarly in four patients with penile SCC cancer, the NCM of the present invention was used and was followed by chemotherapy with 5FU and cysplatinum and a second cycle of the NCM of the present invention. Clinical tumor reduction was observed with the initial immunotherapy and with the chemotherapy and examination of the tumor from surgery showed persistence of the immune regression. Another patient with H&N SCC treated with the NCM of the present invention followed by chemotherapy with 5FU and cisplatinum showed the same result. These observations indicate that the NCM of the present invention can be used with chemotherapy.

Figure 11:
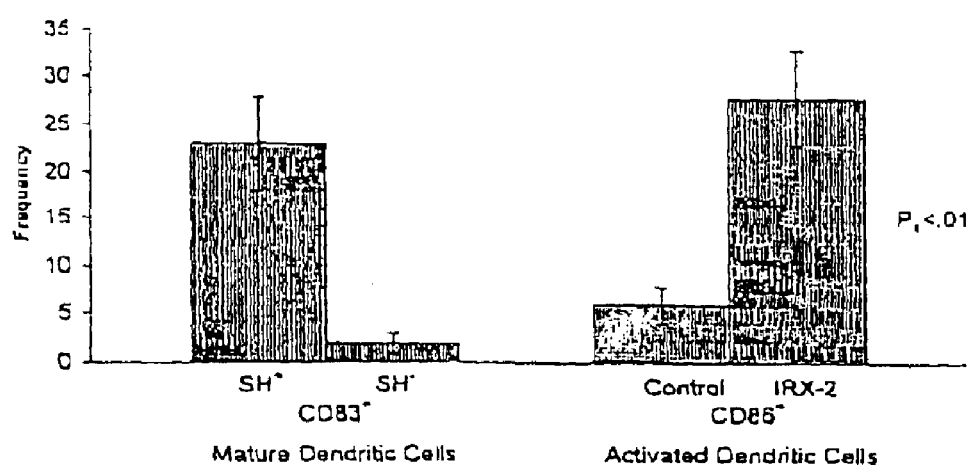
FIG. 11 is a dendritic cell graph illustrating the effects of NCM treatment on mature and activated dendritic cells.

Example 11
Further Characterization of the Correction by the NCM of the Dendritic Cell Defect in Cancer:

Lymph nodes from five, NCM treated patients and five, untreated H & N SCC control patients were isolated and cellular constituents analyzed by flow cytometry using a panel of cell surface markers for dendritic cells (i.e., CD83, CD86, and CD 68). Sinus histiocytosis (SH+) is associated with an accumulation of CD68+, CD83+, but CD86-DC's while those without noticeable SH have few CD83+cells (FIG. 11). NCM treatment of the present invention results in a five-times increase in the number of CD86+(concomitant with CD68+CD83+) cells compared to non-treated cancer controls, indicating a conversion to an "activated" DC phenotype. Controls are untreated H & N SCC compared to NCM treated cancer patients.

Sinus histiocytosis is characterized by and intrasinusoidal accumulate on of $CD68^+$ $CD83^+$ $CD86^-$ myeloid dendritic cells (DC) and effective use of the NCM of the present invention was associated with a 5-fold increase in $CD86^+$ cells indicative of activated mature DC. Sinus histiocytosis is confirmed to represent an accumulation of partially matured DC presumed to be bearing endogenous tumor peptides. Full maturation and activation with expression of the co-stimulatory receptor (B7.1 or CD86) reflects use of the NCM of the present invention to correct this defect on maturation and to allow effective antigen presentation to T-cells. The NCM of the present invention reverses sinus histiocytosis and lead to effective immunization of "naive" T-cells.

The fact that sinus histiocytosis is characterized by a defect in DC of myeloid origin and the negative NCM skin test predicts a defect in another myeloid cell, the monocyte suggests that these are linked observations (i.e., there exist a myeloid lineage defect that is crucial to host immune response to cancer).

Example 12
Administration of Exogenous Tumor Antigens Using the Invention Mice:

The procedure was to immunize mice with Prostate Specific Membrane Antigens (PSMA) as T Cell Peptides (ALF & LLH) (100 µg@) conjugated to either OVALBUMIN or Keyhole Limpet Hemocyanin (KLH). Previous attempts with isolated unconjugated peptides were not successful in mice. NCM (0.1 mL) was given as a single immunization with both conjugated antigens preceded by low dose CY (400 µg/mouse) followed by 9 daily injections of NCM (0.1 mL) without antigens, while CpG, Alum, or Ribi-Corixa adjuvants were a single primary immunization with the OVA conjugate. Two booster immunizations (conjugate plus adjuvant) were given at day 21 and 28 to each group of mice. DTH to the T cell peptides was measured 9 days after the final boost and serum was taken at sacrifice on days 15–21.

Figure 12:
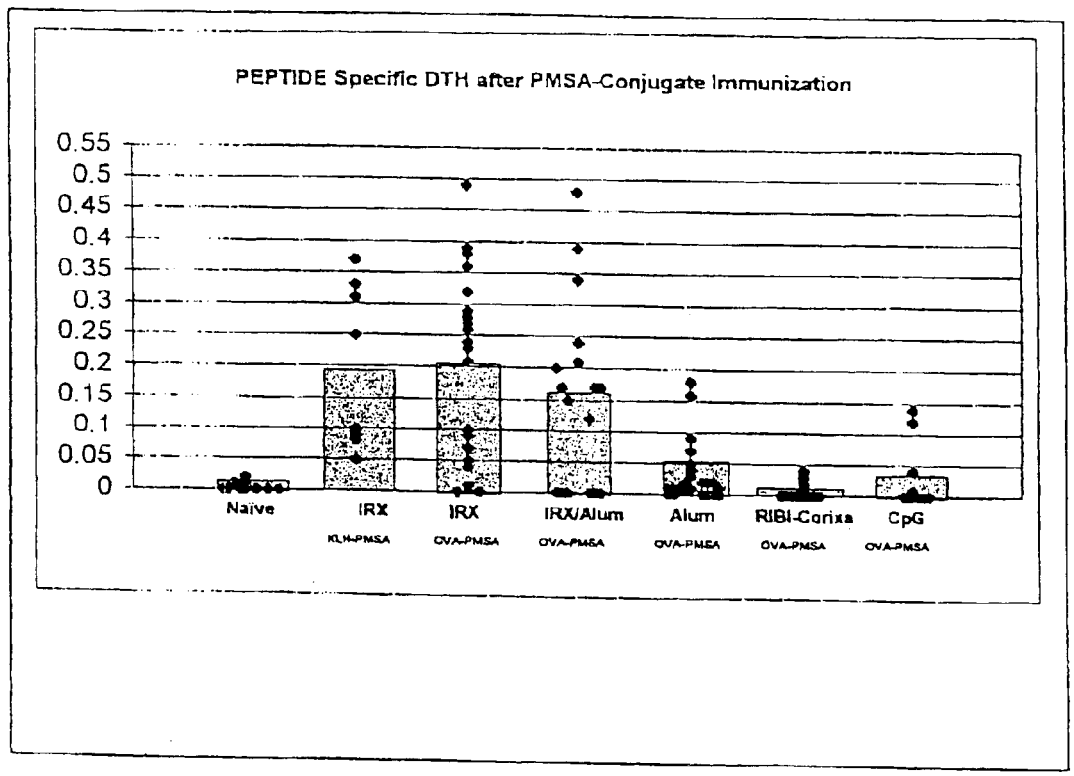
FIG. 12 is a chart illustrating peptide specific DTH response of mice immunized with conjugate and adjuvants, wherein the response is indicated as swelling in mm for individual mice (dots) and for the average (bar), the adjuvant is listed on the x-axis, naive indicates mice not immunized, and all other mice are immunized with Ovalbumin-PSMA peptide conjugates except where indicated (KLH).

FIG. 12 shows the DTH results to skin testing with the individual ALF and LLH peptides (10μg@) without conjugate. NCM induces significant DTH responses following immunization with both conjugates and with Alum for the OVA conjugate. Alum, Ribi-Corixa, and CpG showed negligible activity.

Serum Antibody Results:

Serum was diluted as indicated and added to the wells of a microplate coated with either peptide (ALF or LLH) or ovalbumin. Results are expressed as the average OD at 405 for 5 mice groups. Data are presented in Table VII.

Mice immunized with KLH conjugate+NCM were negative for Ovalbumin antibodies, but positive for the peptides. Mice immunized with OVA conjugates+NCM were positive for antibodies for both OVA and the peptides, while those immunized with OVA conjugate+CpG were positive for OVA only. These results indicate that NCM makes conjugated PMSA peptides effective at stimulating both DTH and IgG responses specific for the peptides, while other adjuvants like alum, Ribi-Corixa, and CpG were inactive or poorly active.

Humans:

Three patients with advanced prostate cancer received unconjugated ALF & LLH peptides (100 μg @) with NCM (1 ml-100 units IL-2 equivalence) preceded by low dose CY (300 mg/m$^2$) and daily INDO (25 mg tid) plus 9 additional injections of NCM (1 ml). On day 15, a booster of NCM plus peptides was given. One patient (#4) received OVA conjugated peptides in this regimen. Delayed hypersensitivity reactions (DTH) were measured with NCM (0.1 ml), ALF, LLH (10 μg) by intradermal skin test read at 24 hours in centimeters of erythema and in duration. The results are presented in Table VII.

TABLE VII

DTH to PSMA peptides & NCM

|  |  | Time 0 | 1 month |
|---|---|---|---|
| NCM | 1) | 0 | 0.5 |
|  | 2) | 1.0 | 1.0 |
|  | 3) | 0.5 | 1.0 |
|  | 4) | 0.3 | 0.3 |
| ALF Peptide | 1) | 0 | 0.5 |
|  | 2) | 0 | 0.1 |
|  | 3) | 1.0 | 1.0 |
|  | 4) | 0 | 0.4 |
| LHH peptide | 1) | 0 | 0.5 |
|  | 2) | 0 | 0.3 |
|  | 3) | 1.5 | 2.0 |
|  | 4) | 0 | 0.5 |

These data indicate that the NCM regimen is effective in inducing DTH reactions to unconjugated and conjugated PMSA peptides in humans with advanced prostate cancer. This result is different from results of most prior attempts that have failed with isolated peptides.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

U.S. Pat. Nos.
4,116,951
4,353,821
4,390,623
4,439,196
4,447,224
4,447,233
4,464,355
4,466,918
4,470,926
4,475,196
4,486,194
4,487,603
4,612,365
4,910,296
4,925,678
4,959,217
5,100,664
5,167,616
5,169,383
5,225,182
5,503,841
5,632,983
5,643,565
5,698,194
5,800,810
6,060,068

Publications

Albert et al, Nature, Vol. 392, pp. 86–89 (1998).

Banchereau et al, Annual Reviews of Immunology, Vol. 18, pp. 767–811 (2000).

Barrera J, Verastegui E, Meneses A, de la Garza J, Zinser J & Hadden J W. Neoadjuvant immunological treatment with IRX-2 in patients with advanced oral cavity squamous cell carcinoma of the head and neck induces clinical and histological responses. In First World Congress on Head and Neck Oncology. J J Alvarez Vicent, Ed. Monduzzi, Bologna, Italy; 1998; pp 1017–1019

Barrera J, Verastegui E, Meneses A, Zinser J, de la Garza J, Hadden J W. Combination immunotherapy of squamous cell head and neck cancer: A phase 11 trial. Arch Otolaryngol Head Neck Surg 126:345–351 (2000).

Bellone, et al, Immunology Today, Vol 20, No.10, p 457–462 (1998).

Berd D, Mastrangelo M J. Effect of low dose cyclophosphamide on the immune system of cancer patients: reduction of T suppressor function without depletion of the CD8+subset. Cancer Research 47:3317–3321 (1987).

Berd D. Low doses of chemotherapy to inhibit suppressor T cells. Progress in Clin Biol Res 288:449458 (1989).

Borysiewickz L K, Fiander A. Nimako M. A recombinant vaccine virus encoding human papilomavirus type 16 and 18, E6 and E7 proteins as immunotherapy for cervical cancer. Lancet 347:1524–1527 (1996).

Burke and Olson, "Preparation of Clone Libraries in Yeast Artificial-Chromosome Vectors" in Methods in Enzymology, Vol. 194, "Guide to Yeast 'Genetics and Molecular Biology", eds. C. Guthrie and G. Fink, Academic Press, Inc., Chap. 17, pp.251–270 (1991).

Capecchi, "Altering the genome by homologous recombination" Science 244:1288–1292 (1989).

Cortesina G, DeStefani A, Galcazzi E. Temporary regression of recurrent squamous cell carcinoma of the head and neck is achieved with a low dose but not a high dose of recombinant interleukin 2 injected perilymphatically. Br J Cancer 69:572–577 (1994).

Cortesina G, DeStefani A, Giovarelli M, et al. Treatment of recurrent squamous cell carcinoma of the head and neck with low doses of interleukin-2 injected perilymphatically. Cancer 62:2482–2485 (1988).

Cortesina G, Destefani A & Galeazzi E. Temporary regression of recurrent squamous cell carcinoma of the head and neck is achieved with a low but not high dose of recombinant interleukin-2 injected perilymphatically. Br. J. Cancer; 1994; 69: 572–577.

Cregg J M, Vedvick T S, Raschke W C: Recent Advances in the Expression of Foreign Genes in Pichia pastoris, Bio/Technology 11:905–910 (1993).

Cross D S, Platt J L, Juhn S K, et al. Administration of a prostaglandin synthesis inhibitor associated with an increased immune cell infiltrate in squamous cell carcinoma of the head and neck. Arch Otolaryngol Head Neck Surg 1992; 118: 526-8

Culver, Site-Directed recombination for repair of mutations in the human ADA gene. (Abstract) Antisense DNA & RNA based therapeutics (1998).

Davies et al., "Targeted alterations in yeast artificial chromosomes for inter-species gene transfer", Nucleic Acids Research, Vol. 20, No. 11, pp. 2693–2698 (1992).

DeLaugh and Lofts, Current Opinion In Immunology, Vol. 12, pp. 583–588 (2000).

DeStefani A, Forni G, Ragona R, et al. Improved survival with perilymphatic interleukin 2 in patients with resectable squamous cell cancer of the inner cavity and oropharynx. Cancer 2002; 95: 90–97

Dickinson et al., "High frequency gene targeting using insertional vectors", Human Molecular Genetics, Vol. 2, No. 8, pp.1299–1302 (1993).

Duff and Lincoln, "Insertion of a pathogenic mutation into a yeast artificial chromosome containing the human APP gene and expression in ES cells", Research Advances in Alzheimer's Disease and Related Disorders (1995).

Gilboa, E, Eglitis, M A, Kantoff, P W, Anderson, W F: Transfer and expression of cloned genes using retroviral vectors. BioTechniques 4(6):504–512 (1986). Gillis et al. (1978)

Hadden J W, Endicott J, Baekey P, Skipper P, Hadden E M. Interleukins and contrasuppression induce immune regression of head and neck cancer. Arch Otolaryngol Head Neck Surg. 120:395–403 (1994).

Hadden J W, Saha A R, Sosa M, Hadden E M. Immunotherapy with natural interleukins and/or Thymosin α1 potently augments T lymphocyte responses of hydrocortisone-treated aged mice. Int'l J Immunopharmacol 17:821–828 (1995).

Hadden J W. Immunology and immunotherapy of breast cancer: An update: Int'l J Immunopharmacol 21:79–101 (1999).

Hadden J W. The immunopharmacology of head and neck cancer: An update. Int'l J Immunopharmacol 11/12:629–644 (1997).

Hadden J W. The treatment of zinc deficiency is an immunotherapy. Int'l J Immunopharmacol 17:696–701 (1995).

Hadden, J., E. Verastegui, J. L. Barrera, M. Kurman, A. Meneses, J. W. Zinser, J. de la Garza, and E. Hadden, "A trial of IRX-2 in patients with squamous cell carcinomas of the head and neck," International Immunopharmacology 3; 1073–1081 (2003).

Hank A J, Albertini M R, Sondel P M. Monoclonal antibodies, cytokines and fusion proteins in the treatment of malignant disease. Cancer Chemother & Biol Resp Mod 18:210–222 (1999).

Hirsch B, Johnson J T, Rabin B D, et al. Immunostimulation of patients with head and neck cancer. Arch Otolaryngol 1983; 109: 298–301

Huston et al, "Protein engineering of single-chain Fv analogs and fusion proteins" in Methods in Enzymology (J J Langone, ed.; Academic Press, New York, N.Y.) 203:46–88 (1991).

Huxley et al., "The human HPRT gene on a yeast artificial chromosome is functional when transferred to mouse cells by cell fusion", Genomics, 9:742–750 (1991).

Jakobovits et al., "Germ-line transmission and expression of a human-derived yeast artificial chromosome", Nature, Vol. 362, pp. 255–261 (1993).

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99 (1989).

Kavanaugh D Y, Carbone D P. Immunologic dysfunction in cancer. Hematol-Oncol Clinics of North Amer 10(4):927–951 (1996).

Lamb et al., "Introduction and expression of the 400 kilobase precursor amyloid protein gene in transgenic mice", Nature Genetics, Vol. 5, pp. 22–29 (1993).

Maass G, Schmidt W, Berger M, et al. Priming of tumor-specific T-cells in the draining lymph nodes after immunization with interleukin 2-secreting tumor cells: three consecutive stages may be required for successful tumor vaccination. Proc Natl Acad Sci USA, 92:5540–5542 (1995).

Mackall (Stem Cells 2000, Vol. 18. pp. 10–18) Mackall et al, (New England Journal of Medicine, Vol. 332, pp. 143–149 (1995).

Maclean G D, Miles D W, Rubens R D, Reddish M A, Longenecker bone marrow. Enhancing the effect of Theratope STn-KLH cancer vaccine in patients with metastatic breast cancer by pretreatment with low-dose intravenous cyclophosphamide. J Immunother Emphasis Tumor Immunol 19(4):309–316 (1996).

Marshak et al, "Strategies for Protein Purification and Characterization. A laboratory course manual." CSHL Press (1996). Mastrangelo M J, Maguire H C Jr., Sato T, Nathan F E, Berd D. Active specific immunization in the treatment of patients with melanoma. (Review) Seminars in Oncology 23(6):773–781 (1996).

Meneses A, Verastegui E, Barrera J L, Zinser J, de la Garza J, Hadden J W. Histological findings in patients with head and neck squamous cell carcinoma receiving perilympatic natural cytokine mixture prior to surgery. Arch Pathol Lab Med 122:447–454 (1998).

Meneses A, Verastegui E, Barrera J L, de la Garza J, and Hadden J W, "Lymph node histology in head and neck cancer: impact of immunotherapy with IRX-2," International Immunopharmacology, 3; 1083–1091 (2003).

Mernaugh and Mernaugh, "An overview of phage-displayed recombinant antibodies" in Molecular Methods In Plant Pathology (R P Singh and U S Singh, eds.; CRC Press Inc., Boca Raton, Fla.) pp. 359–365 (1995).

Mishell and Shiigi (Selected Methods in Cellular Immunology (1981).

Montovani A, Sozzani S, Locati M, et al. Macrophage polarization: tumor associated macrophages as a paradigm for polarized M2 mononuclear phagocytes. Trends in Immunol 2002; 23: 549–555

Murphy G P, Tjoa B A, Simmons S J. The prostate. 38:43–78 (1999).

Panje W R. Regression of head and neck carcinoma with a prostaglandin-synthesis inhibitor. Arch Otolaryngol 1981; 107: 658–63

Pearson and Choi, Expression of the human b-amyloid precursor protein gene from a yeast artificial chromosome in transgenic mice. Proc. Natl. Acad. Sci. USA, 90:10578–82 (1993).

Roitt I, Brostoff J, Male D. Immunology, J B Lippincott Co, Phila, Pa., (1989).

Rothstein, "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281–301 (1991).

Saha A, Hadden E M, Hadden J W. Zinc induces thymulin secretion from human thymic epithelial cells in vitro and augments splenocytes and thymocyte response in vivo. Int'l J Immunopharmacol 17:729–734 (1995).

Sahin U, Tureci 0, Pfreundschuh. Serological identification of human tumor antigens. Curr Opin Immunol 9:709–715 (1997).

Sanda M G, Smith D C, Charles L G. Recombinant vaccinia-PSA (Prostvac) can include a prostate-specific immune response in androgen-modulated human prostate cancer. Urology 52:2 (1999).

Schedl et al., "A yeast artificial chromosome covering the tyrosinase gene confers copy number-dependent expression in transgenic mice", Nature, Vol. 362, pp. 258–261 (1993).

Sprent, et al, Science, Vol. 293, 245–248 (2001).

Strauss et al., "Germ line transmission of a yeast artificial chromosome spanning the murine a1 (I) collagen locus", Science, Vol. 259, pp.1904–1907 (1993).

Tagawa M. Cytokine therapy for cancer. Current Pharmaceut Design 6(6):681–699 (2000).

Valente G, DeStefani A, Jemma C, Giovarelli M, Geuna N, Cortesina G, Forni G, Palestro G. Infiltrating leukocyte populations and T-lymphocyte subsets in head and neck squamous cell carcinomas from patients receiving perilymphatic injections of recombinant interleukin-2. A pathologic and immunophenotypic study. Modern Pathol 3(6):702–708 (1990).

Valente G, DeStefani A, Jemma C. Infiltrating leukocyte populations and T lymphocyte subsets in H&N SCC from patients receiving perilymphatic injections of rIL-2. Mod Pathol 1990; 3: 702–708

Van der Eynde B, Van der Bruggen, T cell defined tumor antigens. Curr Opin Immunol 9:684–693 (1997).

Verastegui E, Barrera J L, Zinzer J, del Rio R, Meneses A, de la Garza J, Hadden J W. A natural cytokine mixture (IRX-2) and interference with immune suppression induce immune mobilization and regression of head and neck cancer. Int'l J Immunopharmacol 11/12:619–627 (1997).

Verastegui E, Hadden E M, Barrera J, Meneses A, Hadden J W. A natural cytokine mixture (IRX-2) and interference with immune suppression induce immune regression and improved survival in head and neck cancer. Int'l. Journal of Immunorehabilitation; 1999; 12: 5–11.

Wang R F, Rosenberg S A. Human tumor antigens for cancer vaccine development. Immunologic Reviews 170:85–100 (1999).

Weber J. Tumor vaccines. Medscape Anthology 3:2 (2000).

Whiteside, et al, Cancer Res. 53:5654–5662, (1993).

Wolf et al, Arch. Oto. Laryngol. 111:716–725 (1985).

What is claimed is:

1. A synergistic anti-cancer composition comprising an effective amount of cyclophosphamide (CY); an effective amount of indomethacin (INDO); and an effective amount of a cytokine mixture including cytokines selected from the group consisting essentially of IL-I, ILg-2, IL-6, IL-8, IL-12, IFN-alpha, TNF-alpha, GM-CSF, G-CSF, wherein the cytokines can be naturally made, recombinants thereof, or a mixture of naturally made and recombinants thereof.

* * * * *